(12) United States Patent
Akira et al.

(10) Patent No.: US 7,078,585 B1
(45) Date of Patent: Jul. 18, 2006

(54) BACTERIAL CELL COMPONENT-UNRESPONSIVE MODEL MOUSE

(75) Inventors: Shizuo Akira, Mino (JP); Osamu Takeuchi, Mino (JP); Kiyoshi Takeda, Mino (JP)

(73) Assignee: Japan Science and Technology Agency, Saitama (JP)

( * ) Notice: Subject to any disclaimer, the term of this patent is extended or adjusted under 35 U.S.C. 154(b) by 0 days.

(21) Appl. No.: 09/889,324

(22) PCT Filed: Jan. 13, 2000

(86) PCT No.: PCT/JP00/00132

§ 371 (c)(1),
(2), (4) Date: Jul. 13, 2001

(87) PCT Pub. No.: WO00/41561

PCT Pub. Date: Jul. 20, 2000

(30) Foreign Application Priority Data

Jan. 14, 1999 (JP) .............................. H11-007365
Aug. 12, 1999 (JP) .............................. H11-228282
Oct. 29, 1999 (JP) .............................. H11-309238

(51) Int. Cl.
*A01K 67/027* (2006.01)

(52) U.S. Cl. .......................................... 800/18; 800/3
(58) Field of Classification Search .................... 800/3, 800/18, 22; 435/252.1
See application file for complete search history.

(56) References Cited

OTHER PUBLICATIONS

Vacheron et al. Induction of interleukin 1 secretion by adjuvant-active peptidoglycans. Infection and Immunity, 1983, vol. 42, No. 3. pp. 1049-1054.*
Bradley et al. Modifying the Mouse: Design and Desire. May 1992. Biotechnology. vol. 10, pp. 534-539.*
Campbell and Wilmut. Totipotency or Multipotentiality of Cultured Cells: Applications and Progress. Theriogenology. Jan. 1, 1997. vol. 47, No. 1, pp. 63-70.*
Mullins and Mullins. Perspective Series: Molecular Medicine in Genetically Engineered Animals. Apr. 1, 1996. Clinical Investigation. vol. 97, No. 7, pp. 1557-1560.*
Sigmund. Viewpoint: Are Studies in Genetically Altered mice Out of Control? Jun. 2000. Arterioscler Thromb. Vasc. Biol. vol. 20. pp. 1425-1429.*
Takeuchi, Osamu et al., Differential Roles of TLR2 and TLR4 in Recognition of Gram-Negative and Gram-Positive Bacterial Cell Wall Components, Immunity, vol. 11, 443-451, Oct., 1999 by Cell Press, Japan.
Hashimoto, Carl et al., The Toll Gene of *Drosophila*, Required for Dorsal-Ventral Embryonic Polarity, Appears to Encode a Transmembrane Protein, Cell, vol. 52, 269-279, Jan. 29, 1988 by Cell Press, Dept. of Molecular Biology, University of California, Berkeley, California.
Belvin, Marcia P. et al., A Conserved Signaling Pathway: The *Drosophila* Tool-Dorsal Pathway, Annu. Rev. Cell Div. Biol. 1996. 12:393-416, 1996 by Annual Reviews Inc., Genetic Division, Dept. of Molecular and Cell Biology, University of California, Berkeley, California.
Adachi, Osamu et al., Targeted Disruption of the MYD88 Gene Results in Loss of IL-1-and IL-18-Mediated Function, Immunity, vol. 9, 143-150, Jul. 1998 by Cell Press, Core Research for Evolutional Science and Technology Japan Science and Technology Corporation.

(Continued)

*Primary Examiner*—David Guzo
*Assistant Examiner*—Celine Qian
(74) *Attorney, Agent, or Firm*—Ann S. Hobbs; Robert Kinberg; Venable LLP

(57) ABSTRACT

A knockout mouse which is unresponsive to peptidoglycan, a lipoprotein/lipopeptide and the like, and is useful for elucidating the contribution of individual members of the TLR family to a signaling stimulated with bacterial cell components in vivo, in particular, the role of TLR2 and MyD88 in vivo. A bacterial cell component-unresponsive knockout mouse is generated by a process comprising the steps of: a targeting vector is constructed by replacing a whole or a part of a gene fragment of an exon region containing a cytoplasmic region of TLR2 or MyD88 gene and the like with a plasmid having a poly A signal and a marker gene; the targeting vector is introduced into an embryonic stem cell; the targeting embryonic stem cell having a homologously recombined TLR2 or MyD88 gene is microinjected into the blastocyst of a mouse and the blastocyst is put back into the uterus of a recipient mouse.

11 Claims, 21 Drawing Sheets

OTHER PUBLICATIONS

Lemaitre, Bruno et al., The Dorsoventral Regulatory Gene Cassette Spatzle/Toll/Cactus Controls the Potent Antifungal Response in *Drosophila* Adults, Cell, vol. 86, 973-983, Sep. 20, 1996 by Cell Press, Institute de Biologie Moleculaire et Cellulaire, France.

Hatfield, Craig Bond et al., Scientific Correspondence, Nature, vol. 351, 355-356, May 30, 1991.

O'Neill, Luke A. et al., Signal Transduction Pathways Activated by the IL-1 Receptor Family: Ancient Signaling Machinery in Mammals, Insects and Plants, Journal of Leukocyte Biology, vol. 63, Jun. 1998, Dept. of Biochemistry and the National Pharmaceutical Biotechnology Center, Trinity College, Dublin, Ireland.

Lemaitre, Bruno et al., *Drosophila* Host Defense: Differential Induction of Antimicrobial Peptide Genes After Infection by Various Classes of Microorganisms, Proc. Natl. Acad. Sci. USA, vol. 94, pp. 14614-14619, Dec., 1997, Immunology.

Williams, Michael J. et al., The 18-Wheeler Mutation Reveals Complex Antibacterial Gene Regulation in *Drosophila* Host Defense, The EMBO Journal, vol. 16 No. 20, pp. 6120-1630, 1997, Dept. of Biological Sciences, University of Notre Dame, Notre Dame IN.

Kopp, Elizabeth B. et al., The Toll-Receptor Family and Control of Innate Immunity, Current Opinion in Immunology 11, 13-18, 1999, Section of Immunobiology, Yale University, School of Medicine, New Haven, CT.

Medzhitov, Ruslan et al., A Human Homologue of the *Drosophila* Toll Protein Signals Activiation of Adaptive Immunity, Letters to Nature, 388, pp. 394-397, 1997, Section of Immunobiology, Yale University School of Medicine and Howard Hughes Medical Institute, New Haven Connecticut.

Rock, Fernando L. et al., A Family of Human Receptors Structurally Related to *Drosophila* Toll, Proc. Natl. Acad. Sci. USA, vol. 95, pp. 588-593, Jan. 1998, Developmental Biology, Protein Machine Group, Dept. of Molecular Biology, DNAX Research Institute, Palo Alto, CA.

Chaudhary, Preet M. et al., Cloning and Characterization of Two Tool/Interleukin-1 Receptor-Like Genes TIL3 and TIL-4: Evidence for a Multi-Gene Receptor Family in Humans, Blood, vol. 91, No. 11 (Jun. 1, 1988): pp. 4020-4027, Dept. of Medicine and Molecular Biotechnology, University of Washington, Seattle, WA.

Takeuchi, O. et al., TLR6: A Novel Member of an Expanding Tool-Like Receptor Family, Gene 231, 59-65, 1999, Department of Biochemistry, Hyogo College of Medicine, 1-1 Mukogawa-cho, Hishinomiya, Hyogo 663-8501 Japan.

Muzio, Marta, et al., The Human Tool Signaling Pathway: Divergence of Nuclear Factor KB and JNK/SAPK Activation Upstream of Tumor Necrosis Factor Receptor-Associated Factor 6 (TRAF6), Department of Immunology and Cell Biology, Mario Negri Institute 1-20157 Milau, Italy.

Medzhitov, Ruslan, et al. MYD88 is an Adaptor Protein in the Htoll/il-1 Receptor Family Signaling Pathways, Molecular Cell, vol. 2, 253-258, Aug., 1998, by Cell Press, Section of Immunobiology and Howard Hughes Medical Institue, Yale University School of Medicine, New Haven Connecticut.

Kawai, Taro, et al., Unresponsiveness of MYD88-Deficient Mice to Endotoxin, Immunity, vol. 11, 115-122, Jul. 1999, by Cell Press, Department of Biochemistry, Hyogo College of Medicine, Japan.

Hoshino, Katsuaki et al., Cutting Edge: Toll-Like Receptor 4 (TLR4)-Deficient Mice are Hyporesponsive to Lipopolysaccharide: Evidence for TLR4 as the LPs Gene Product, The American Association of Immunologists, 3749-3752, Department of Biochemistry, Hyogo College of Medicine, Hyogo, Japan.

Heine, Holger et al., Cutting Edge: Cells That Carry a Null Allele for Tool-Like Receptor 2 are Capable of Responding to Endotoxin, The American Association of Immunologists, 6971-6975, 1999, Maxwell Finland Laboratory for Infectious Diseases, Boston University School of Medicine and Boston Medical Center, Boston, MA.

Chow, Jesse C., et al., Toll-Like Receptor-4 Mediates Lipopolysaccharide-Induced Signal Transduction, The Journal of Biological Chemistry, vol. 274, No. 16, Issue or Apr. 16, pp. 10689-10692, 1999, Division of Imflammatory Diseases and Synthetic Chemistry, Boston, MA.

Medzhitov, Ruslan, et al., Innate Immunity: The Virtues of a Nonclonal System of Recognition, Cell, vol. 91, 295-298, Oct. 31, 1997, by Cell Press, Section of Immunobiology, Yale University School of Medicine and Howard Hughes Medical Institute, New Haven, Connecticut.

Morrison, David C. et al., Bacterial Endotoxins and Host Immune Responses, Advances in Immunology, vol. 28, 293-450, 1979, Dept. of Immunopathology, Scripps Clinic Research Foundation, La Jolla, California, West Haven, Connecticut.

Ulevitch, RJ et al., Receptor-Dependent Mechanisms of Cell Stimulation by Bacterial Endotoxin, Annua. Rev. Immunol. 1995. 13:434-457. 1995, by Annual Revies, Inc., Department of Immunology, The Scripps Research Institute, La Jolla California 92037.

Wright, Sameul D. et al., CD 14, A Receptor for Complexes of Lipopolysaccharide (LPS) and LPS Binding Protein, Science, vol. 249, pp. 1431-1433, 1990, Laboratory of Cellular Physiology and Immunology, The Rockefeller University, New York NY.

Kirschning, Carsten J. et al., Human Tool-Like Receptor 2 Confers Responsiveness to Bacterial Lipopolysaccharide, J. Exp. Med., The Rockefeller University Press, vol. 188,No. 11, pp. 2091-2097, Tularik, inc., South San Francisco, CA.

Yang, Ruey-Bing et al., Toll-Like Receptor-2 Mediates Lipopolysaccharide-Induced Cellular Signalling, Nature, vol. 395, 284-288, Sep. 1998.

Yang, Ruey-Bing et al., Signaling Events Induced by Lipopolysaccharide-Activated Toll-Like Receptor 2, The American Association of Immunologists, vol. 163, 639-643, 1999, Department of Molecular Biology, Genetech, Inc., San Franscisco, CA.

Poltorak, Alexander et al., Defective LPS Signaling in C3H/HEJ and C 57BL/105ScCr Mice: Mutations in Tlr4 Gene, Science, vol. 282, p. 2085-2088, J.T. Nguyen, F. E. Cohen, W.A. Lim, Dep. of Cellular and Molecular Pharamacology, San Francisco, CA.

Qureshi, Salman T. et al., Enotoxin-Tolerant Mice Have Mutations in Toll-Like Receptor 4 (Tlr4), J. Exp. Med., The Rockefeller University Press, vol. 189, No. 4, pp. 615-625, Dept. of Medicine, Millennium Pharaceuticals, Inc., Cambridge, MA.

Schwander, Ralf et al., Peptidoglycan-and Lipoteichoic Acid-Induced Cell Activation is Mediated by Toll-Like Receptor 2, The Journal of Biological Chemistry, vol. 274, No. 25, Jun. 18, 1999, pp. 17406-17409, Institute fuer Med. Mikrobiologie, Immunologie und Hygiene, Muenchen, Germany.

Yoshimura, Atsutoshi, et al., Cutting Edge: Recognition of Gram-Positive Bacterial Cell Wall Components by the Innate Immune System Occurs via Toll-Like Receptor, The American Association of Immunologists, Maxwell Finald Laboratory for Infectious, Boston University School of Medicine, Boston, MA.

Muhlradt, Peter F. Isolation, Structure Elucidation, and Synthesis of a Macrophage Stimulatory Lipopeptide From Mycoplasma Fermentans Acting at Picomolar Concentration, J. Exp. Med., The Rockefeller University Press, vol. 185, No. 11, Jun. 2, 1997, 1951-1958, Immunobiology and Structure Research Groups, Gesellschaft fur Biotechnologische Forschtung GmbH, Tubngen, Germany.

Aliprantis, Antonios O. et al., Cell Activation and Apoptosis by Bacterial Lipoproteins Through Toll-Like Receptor-2, Science, vol. 285, 736-739, Jul. 30, 1999, Skirball Institute and Department of Microgiuology, New Yor University School of Medicine, New York, NY.

Brightbill,Hans D., Host Defense Mechanisms Triggered by Microbial Lipoproteins Through Toll-Like Receptors, Science, Jul. 30, 1999, 732-736, vol. 285, Department of Microbiology and Immunology, University of California Los Angeles School of Medicine, Los Angeles, CA 90095.

Denlinger,Loren C., Nucear Translocation of NF-Kb in Lipopolysaccharide=Treated Macrophages Fails to Correspond to Endotoxicity:, Evidence Suggesting a Requirement for a Gamma Interferon-Like Signal, Infection and Immunity, Apr. 1998, 1638-1647, vol. 66, No. 4, Departments of Medical Microbiology and Immunology, Biomolecular Chemistry, Pharmacology, and Medicine, 1330 University Ave., Room 407 SMI, Madison, WI 53706.

Hardiman, Gary, Genetic Structure and Chromosomal Mapping of MYD88, Genomics, 1997, 332-339, Article No. GE974940, Department of Molecular Biology, DNAX Research Institute, Palo Alto California 94304-1104.

Kirschning, Carsten J., Human Toll-Like Receptor 2 Confers Responsiveness to Bacterial Lipopolysaccharide, Dec. 7, 1998, 2091-2097, vol. 188 No. 11, Tularik, Inc., South San Francisco, California 94080.

Gerard, Craig, for Whom the Bell Tolls, News and Views, Sep. 17, 1998, 217,219, vol. 396.

Michalek,Suzanne M. The Primary Role of Lymphoreticular Cells in the Mediation of Host Responses to Bacterial Endotoxim, The Journal of Infectious Diseases, Jan. 1980, 55-63, vol. 141, No. 1, The University of Chicago.

Harbour,Deborah V. Splenic Lymphocyte Production of an Endorphin During Endotoxic Shock, Brain, Begavior, and Immunity, 1987, 123-133, University of Alabama at Birmingham, Birmingham, Alabama 35294.

Ogawa, "Chemical Structure of Lipid A From *Porphyromonas (Bacteroides) gingivalis* Lipopolysaccharide", FEBS 13114, Federation of European Biochemical Societies, vol. 332(1,2):197-201, (1993).

Tanamoto et al., "The Lipid A Moiety Of *Porphyromonas gingivalis* Lipopolysaccharide Specifically Mediates The Activation Of C3H/HeJ Mice", The Journal of Immunology, The American Association of Immunologists, vol. 158:4430-4436, (1997).

Gupta et al., "Peptidoglycan Induces Transcription And Secretion Of TNF-α And Activation of Lyn, Extracellular Signal-Regulated Kinase, And Rsk Signal Transduction Proteins In Mouse Macrophages" The Journal of Immunology, The American Association of Immunologists, vol. 155:2620-2630, (1995).

Heumann et al., "Gram-Positive Cell Walls Stimulate Synthesis Of Tumor Necrosis Factor Alpha And Interleukin-6 By Human Monocytes", Infection and Immunity, American Society for Microbiology, vol. 62(7):2715-1721, (1994).

Barnes et al., "Cytokine Production Inducted By *Mycobacterium tuberculosis* Lipoarabinomannan", The Journal of Immunology, The American Association of Immunologists, vol. 149:541-547, (1992).

Zhang et al., "Mechanisms Of Stimulation Of Interleukin-1β And Tumor Necrosis Factior-α By *Mycobacterium tuberculosis* Components", J. Clin. Invest., The American Society For Clinical Investigation, Inc., vol. 91:2076-2083, (1993).

Kotani et al., "Immunoadjuvant Activities Of Cell Walls And Their Water-Soluble Fractions Prepared From Various Gram-Positive Bacteria", Biken Journal, vol. 18:77-92, (1975).

"Stimulation Of Migration Of Human Monocytes By Bacterial Cell Walls And Muramyl Peptides", Infection And Immunity, American Society For Microbiology, vol. 38(3):817-824, (1982).

Keller et al, "Macrophage Response To Bacteria: Induction Of Marked Secretory And Cellular Activities By Lipoteichoic Acids", Infection And Immunology, American Society For Microbiology, vol. 60(9):3664-3672, (1992).

Pugin et al., "CD14 Is a Pattern Recognition Receptor", Immunity, vol. 1:509-516, (1994).

Gupta et al., "CD14 Is a Cell-Activating Receptor For Bacterial Peptidoglycan", The Journal of Biological Chemistry, vol. 271(38)23310-23316, (1996).

Cleveland et al., "Lipoteichoic Acid Preparations Of GRam-Positive Bacteria Induce Interleukin-12 Through a CD14-Dependent Pathway", Infection And Immunity, American Society For Microbiology, vol. 64(6):1906-1912, (1996).

* cited by examiner

F I G. 5
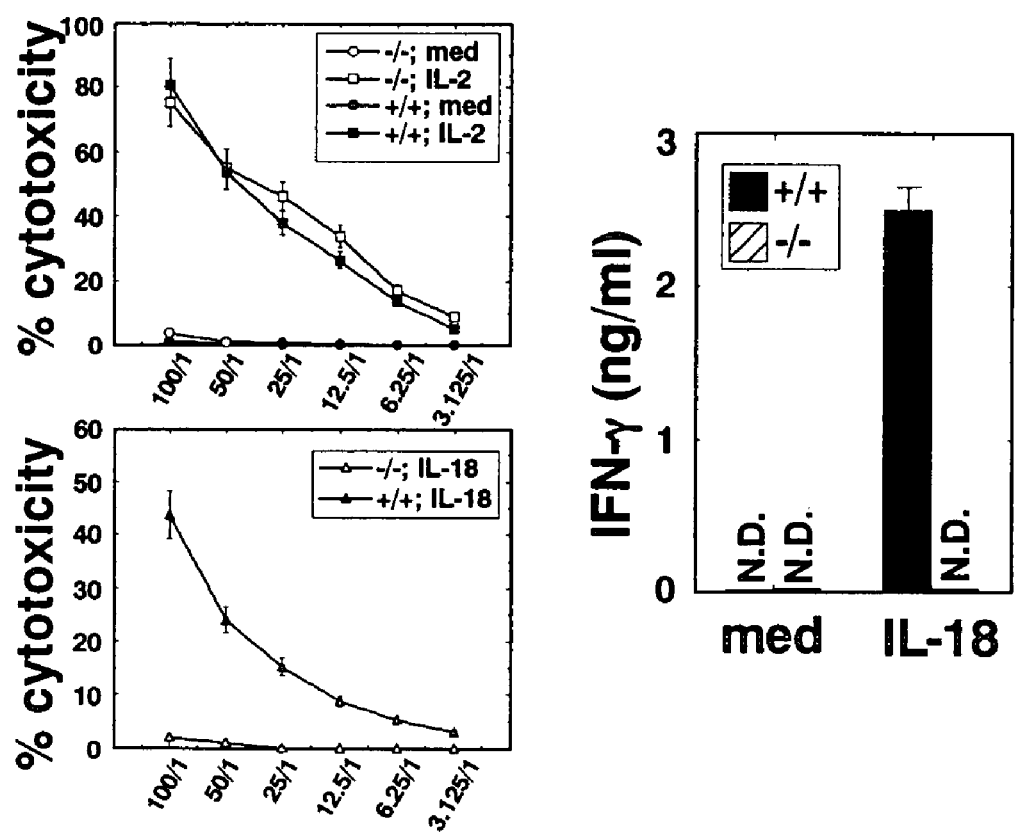

US 7,078,585 B1

BACTERIAL CELL COMPONENT-UNRESPONSIVE MODEL MOUSE

TECHNICAL FIELD

The present invention relates to model non-human animals being unresponsive to a lipoprotein/lipopeptide, which is a cell component of bacteria that belong to *Mycoplasma, Spirochaeta, Escherichia* or the like, and bacterial cell components including peptidoglycan, which is a cell wall fraction of Gram-positive bacteria, and endotoxin, which is a cell wall fraction of Gram-negative bacteria, and further relates to a screening method and the like of a suppressor or a promoter of bacterial infection and an agonist or an antagonist for TLR2 with said bacterial cell component-unresponsive model non-human animals.

BACKGROUND ART

Cytokines are intracellular signal transmitters which play an important role in an immune response, a response upon infection, hematopoiesis, inhibition of virus infection and tumor cells. Among them, a cytokine which transmits signals between lymphocytes is called interleikin (hereinafter, "IL"). Among ILs, IL-1 is a cytokine which mediates various immune responses and inflammatory responses, and is involved in maintenance of homeostasis of living organisms and produced from various cells such as monocytes, macrophages, keratinocytes, vascular endothelial cells and the like when the living organisms get infected or hurt. It has been known that there are two kinds of IL-1, IL-1α and IL-1β, both of which combine to the same receptor. It has been also known that IL-1 exerts its function simultaneously with the activation by an antigen to T cell and by mitogens, makes T cells release IL-2, and enhances the expression of IL-2 receptors to induce T cell proliferation, and that it acts on monocytes and macrophages in order to induce the production of TNF-α, IL-1, IL-6.

IL-1 has two kinds of IL-1 receptors (hereinafter "IL-1R"), and both of the IL-1Rs, type I and type II, have three immunoglobulin-like domains in their extracellular domains. Type I receptors express in T cells and connective tissue, and type II receptors express in splenic B cells, myeloids and the like, and it has been known that type I receptors induce NF-$_\kappa$B in nuclei. It has been also known that there is an IL-1 receptor antagonist (hereinafter "IL-1ra") which shows no bioactivity in spite that it binds to IL-1R with the affinity similar to that of IL-1α and IL-1β, and that it prevents IL-1 from binding to IL-1R competitively.

IL-18 is known to promote the production of interferon-γ (hereinafter "IFN-γ"), to enhance the activation of natural killer cells, to induce the production of IFN-γ from T cells in cooperation of IL-12, and to act an important role in a Th1 (IL-2 producting helper T cells) response. Further, it is known that IL-18 has no structural similarity to IL-12 in spite that it has a functional similarity, and has a structural similarity to IL-1. Moreover, it has been also known that IL-18 is produced as an inactive precursor that requires cleavage by IL-1β-converting enzyme (ICE)/caspase1 for its maturation, as in the case of IL-1β, and that IL-18 activates IL-1R-associated kinase (IRAK) and NF-$_\kappa$B.

A plurality of molecules showing homology to IL-1R have been identified so far, and signal pathways mediated by IL-1R family is being studied intensively now. It has been known that MyD88 is a cytoplasmic protein comprised of an IL-1R homologous domain and a Death domain, and functions as an adaptor molecule which activates NF-$_\kappa$B by recruiting IRAK to IL-1R complex after IL-1 stimulation, and that MyD88 gene was originally separated as a myeloid differentiation primary response gene, which rapidly induces M1 myeloleukemic cells to macrophages by IL-6-stimulated differentiation.

Toxins in bacterial cells being comprised of lipopolysaccharide, which is a major structural component of the outer membrane encompassing peptidoglycan on the surface of Gram-negative bacteria, are called endotoxin, and it has been known that lipopolysaccharide is comprised of lipid called lipid A and various kinds of saccharide which covalently bind to the lipid A. It has been also known that this endotoxin has a bioactivity mainly involved in fever, decrease of leukocytes and platelet, hemorrhagic necrosis of bone marrow cells, hypoglycemia, induction of IFN, activation of B limphocyte (immune response cell derived from marrow), and the like.

It has been known that a Toll gene is required to control dorsoventral patterning during the embryonic development of *Drosophila* (Cell 52, 269–279, 1988, Annu. Rev. Cell Dev. Biol. 12,393–416, 1996), and for antifungal immune responses in adult fly (Cell 86, 973–983, 1996). It has been clarified that the Toll is a type I transmembrane receptor with an extracellular domain containing leucine-rich repeat (LRR) and that its cytoplasmic domain shows high homology to that of mammalian interleukin-1 recepter (IL-1R) (Nature 351,355–356, 1991, Annu. Rev. Cell Dev. Biol. 12, 393–416, 1996, J. Leukoc. Biol. 63, 650–657, 1998). It has been also clarified that another Toll family member, 18-wheeler, participates in the antibacterial host defense but not in the antifungal immune response, and that particular pathogens induce specific antimicrobial immune responses in *Drosophila* through the selective activation of the Toll-pathways (Proc. Natl. Acad. Sci. USA 94, 14614–14619, 1997, EMBO J. 16, 6120–6130, 1997, Curr. Opin. Immunol. 11, 13–18, 1999).

Recently, mammalian homologs of Toll, designated as Toll-like receptors (TLRs), have been identified, and so far, six families including TLR2 and TLR4 have been reported (Nature 388, 394–397, 1997, Proc. Natl. Acad. Sci. USA 95, 588–593, 1998, Blood 91, 4020–4027, 1998, Gene 231, 59–65, 1999). It has been known that the TLR families, as in the case of the IL-1R, recruit IL-1R-associated kinase (IRAK) through the adaptor protein MyD88 as a signal transmitter and activate TRAF 6, and then activate NF-$_\kappa$B in the downstream (J. Exp. Med. 187, 2097–2101, 1998, Mol. Cell 2, 253–258, 1998, Immunity 11, 115–122, 1999). Further, the role of the TLR families in mammals is also believed to participate in innate immune recognition as pattern recognition receptors (PRRs), which recognize bacterial cell common structures (Cell 91, 295–298, 1997).

It has been reported that one of such pathogen-associated molecular patterns (PAMPs) to be recognized by the PRRs is lipopolysaccharide (LPS), a major component of the outer membrane of Gram-negative bacteria (Cell 91, 295–298, 1997), that said LPS stimulates host cells and makes them produce various proinflammatory cytokines including TNF-α, IL-1, and IL-6 (Adv. Immunol. 28, 293–450, 1979, Annu. Rev. Immunol. 13, 437–457, 1995), and that the LPS captured by LPS-binding protein (LBP) is delivered to CD14 on the cell surface (Science 249, 1431–1433, 1990, Annu. Rev. Immunol. 13, 437–457, 1995). However, since CD14 is a glycosylphosphatidylinositol (GPI)-anchored protein without a transmembrane domain, the existence of a bona fide signaling receptor of LPS has been believed.

TLR4, which belongs to the TLR family, is a signaling molecule of LPS, which is a bacterial cell component of Gram-negative bacteria, and transfection of the TLR4 leads to a low constitutive activation of NF$_\kappa$B (J. Exp. Med. 188, 2091–2097, 1998, Nature 395, 284–288, 1998). On the other hand, as TLR2 transmits LPS signal when overexpressed in human embryonic kidney 293 cells in vitro, TLR2 has been thought to be a candidate for the LPS receptor. In addition, Godawski's group has reported that human TLR2 could interact with CD14 to form the LPS receptor complex (J. Immunol. 163, 639–643, 1999). Stimulation treatment with LPS leads to oligomerization of receptors and to subsequent recruitment of IRAK to the receptor complex. In contrast, groups of Poltorak and Qureshi have reported that TLR4 is the causative gene of the LPS hyporesponsiveness of C3H/HeJ mice, that is, the Lps gene, according to positional cloning (Science 282, 2085–2088, 1998, J. Exp. Med. 189, 615–625, 1999).

The inventors of the present invention have found by generation of TLR4-deficient mice that TLR4 is actually involved in LPS signaling (J. Immunol. 162, 3749–3752, 1999). The findings may be attributed to species-specific differences in the primary structure of TLR, in other words, LPS signaling could be mediated by TLR4 in mice and by TLR2 in humans. However, there is a report showing that mouse TLR2 also activated NF-$_\kappa$B in response to LPS (J. Immunol. 162, 6971–6975, 1999). In addition, Chow et al. have reported that they obtained the result showing that human TLR4 activated NF-$_\kappa$B-mediated gene expression by stimulation to LPS/CD14 in a dose-dependent or a time-dependent manner, which is consistent with the observation of C3H/HeJ mice, whereas they obtained the result conflicting with that of Kirschning's group when human 293 cells were used, and they have speculated that the differences of outcome may be due to differences in the lot of 293 cells as well (J. Biol. Chem. 274, 10689–10692, 1999).

Recently, it has been reported that TLR2 may not be involved exclusively in responsiveness to LPS derived from Gram-negative bacteria (J. Immunol. 162, 6971–6975, 1999) but may also act as a signaling receptor for peptidoglycan (PGN) and lipoteichoic acid (LTA) from Gram-positive bacteria, which have another common bacterial structural pattern (J. Biol. Chem. 274, 17406–17409, 1999, J. Immunol. 163, 1–5, 1999). Further, it has been also reported that whole Gram-positive bacteria, soluble PGN, and LTA induced the activation of NF-$_\kappa$B in 293 cells expressing TLR2, but not induced the activation of NF-$_\kappa$B in the cells expressing TLR1 or TLR4 (J. Biol. Chem. 274, 17406–17409, 1999). Still further, it has been also reported that Chinese hamster ovary (CHO) fibroblast cells which express human TLR2 but not TLR4 were activated similarly by heat-killed *Staphylococcus aureus* and *Streptococcus pneumoniae*, and PGN derived from *Staphylococcus aureus* (J. Immunol. 163, 1–5, 1999).

Mycoplasmas, known as pathogens in animals and humans, are wall-less bacteria, yet they are capable of activating macrophages. A number of reports have identified this macrophage-activating material as lipoproteins/lipopeptides, and one of these lipopeptides, the 2 kD macrophage-activating lipopeptide MALP-2 derived from *Mycoplasma fermentans*, was biochemically fully characterized and has become available by synthesis (J. Exp. Med. 185:1951, 1997). It is known that the lipid moiety has 2 asymmetric C atoms, and that the synthetic MALP-2 comprised of the S, R racemate had a specific activation similar to the natural compound action at picomolar concentrations in vitro. Little is known about the signal pathways or the cell-surface receptors for MALP-2, except that MALP-2 activates NF-$_\kappa$B.

It is reported that lipoproteins/lipopeptides from mycobacterium and *Borrelia burgdorferi* induced the activation of host cells through TLR2 in vitro (Science 285, 736–739, 1999, Science 285, 732–736, 1999). Nevertheless, the conclusions obtained from overexpression experiments do not necessarily reflect the function of TLR family in vivo. It is also reported that the results of analysis of the responsiveness based on NF-$_\kappa$B activation are not related to biological responses mediated by these stimuli (Infect. Immun. 66, 1638–1647, 1998).

In addition, it is known that the function of a specific gene can be analyzed in individual level by using transgenic mice in which genes are artificially introduced and expressed, and gene-deficient mice generated by gene targeting in which specific genes on genomes are artificially transformed by homologous recombination with embryonic stem cells (hereinafter "ES cells"). In general, gene-deficient mice are called knockout mice, and TLR2 knockout mice and MyD88 knockout mice have not been known, and moreover, it has not been known that TLR2 knockout mice and MyD88 knockout mice are unresponsive to bacterial cell components, either.

SUMMARY OF THE INVENTION

Though in vivo responses to bacterial cell components are expected to vary depending on the difference of expression levels of each TLR on the cell surface, the contribution of individual members of the TLR family and MyD88, the adaptor protein of the TLR family, to signaling by bacterial cell components' stimuli in vivo remains to be elucidated. An object of the present invention is to provide model non-human animals being unresponsive to a lipoprotein/lipopeptide, a cell component of bacteria which belong to *Mycoplasma, Spirochaeta, Escherichia* or the like, bacterial cell components including peptidoglycan, which is a cell wall fraction of Gram-positive bacteria, and endotoxin, which is a cell wall fraction of Gram-negative bacteria and the like, for example, non-human animals whose function of TLR2 and MyD88 genes is deficient on their chromosomes, which are useful for elucidating the contribution of individual members of the TLR family and MyD88, the adaptor protein of the TLR family, to signaling by bacterial cell components' stimuli in vivo, in particular, the role of TLR2 and MyD88 in vivo, and to provide a screening method and the like of a suppressor or a promoter of bacterial infection and an agonist or an antagonist for TLR2 with said bacterial cell component-unresponsive model non-human animals.

The inventors of the present invention have conducted intensive study for attaining the object. They generated TLR2 or MyD88 gene-deficient mice as follows: an exon region including a cytoplasmic region of TLR2 gene or two exon regions encoding the C-terminal portion of MyD88 are replaced with the neomycin-resistant gene respectively by homologous recombination with plasmid vectors in ES cells and HSV-tk gene was induced into each C-terminal side respectively, and ES cell clones doubly resistant of G418 and gancyclovir were screened; the ES cell clones were microinjected into blastocysts of C57BL/6 mice; TLR2 or MyD88 knockout mice whose function of TLR2 or MyD88 genes is deficient on their chromosomes were born through the germline at the expected Mendelian ratios. Then the inventors have found that those TLR2 or MyD knockout mice are transgenic mice which grow healthy and show no obvious abnormalities until 20 weeks of age, and that those TLR2 or MyD knockout mice are unresponsive to peptidoglycan, which is a cell wall component of Gram-positive bacteria and to a lipoprotein/lipopeptide and other such bacterial cell components, and the present invention has thus completed.

The present invention relates to a model non-human animal being unresponsive to bacterial cell components characterized in being unresponsive to a lipoprotein/lipopeptide, which is a bacterial cell component (claim 1), the model non-human animal being unresponsive to bacterial cell components according to claim 1, wherein a lipoprotein/lipopeptide is a macrophage-activating lipopeptide derived from bacteria which belong to *Mycoplasma* (claim 2), the model non-human animal being unresponsive to bacterial cell components according to claim 1 or 2, wherein the model non-human animal is unresponsive to peptidoglycan, which is a bacterial cell component (claim 3), the model non-human animal being unresponsive to bacterial cell components according to any one of claims 1 to 3, wherein the model non-human animal is hyporesponsive to a cell wall fraction of Gram-positive bacteria (claim 4), the model non-human animal being unresponsive to bacterial cell components according to any one of claims 1 to 4, wherein the model non-human animal is unresponsive to endotoxin, which is a bacterial cell component (claim 5), the model non-human animal being unresponsive to bacterial cell components according to any one of claims 1 to 5, wherein the model non-human animal is unresponsive to lopoteichoic acid, which is a bacterial cell component (claim 6), the model non-human animal being unresponsive to bacterial cell components according to any one of claims 1 to 6, wherein the model non-human animal is unresponsive to *Mycobacterium tuberculosis* lysate, which is a bacterial cell component (claim 7), the model non-human animal being unresponsive to bacterial cell components characterized by that the model non-human animal being unresponsive to bacterial cell components according to any one of claims 1 to 4 is a non-human animal whose function of TLR2 gene is deficient on its chromosome (claim 8), the model non-human animal being unresponsive to bacterial cell components characterized by that the model non-human animal being unresponsive to bacterial cell components according to any one of claims 1 to 7 is a non-human animal whose function of MyD88 gene is deficient on its chromosome (claim 9), the model non-human animal being unresponsive to bacterial cell components according to any one of claims 1 to 9, wherein the non-human animal is a rodent (claim 10), and the model non-human animal being unresponsive to bacterial cell components according to claim 10, wherein the rodent is a mouse (claim 11).

The present invention also relates to a screening method of a suppressor or a promoter of responsiveness to bacterial cell components characterized in comprising the steps of: macrophages or splenocytes obtained from the non-human animal being unresponsive to bacterial cell components and a subject material are brought into contact in advance in vitro; the macrophages or the splenocytes are cultured in the presence of bacterial cell components; the macrophage activity level or the splenocyte activity level of the macrophages or of the splenocytes is measured and assessed, a screening method of a suppressor or a promoter of responsiveness to bacterial cell components characterized in comprising the steps of: macrophages or splenocytes obtained from the non-human animal being unresponsive to bacterial cell components and bacterial cell components are brought into contact in advance in vitro; the macrophages or the splenocytes are cultured in the presence of a subject material; the macrophage activity level or the splenocyte activity level of the macrophages or of the splenocytes is measured and assessed, a screening method of a suppressor or a promoter of responsiveness to bacterial cell components characterized in comprising the steps of: a subject material is administered in advance to the non-human animal being unresponsive to bacterial cell components; macrophages or splenocytes obtained from the non-human animal are cultured in the presence of bacterial cell components; the macrophage activity level or the splenocyte activity level of the macrophages or of the splenocytes is measured and assessed, a screening method of a suppressor or a promoter of responsiveness to bacterial cell components characterized in comprising the steps of: a subject material is administered in advance to the non-human animal being unresponsive to bacterial cell components; the non-human animal is made to be infected with bacteria; the macrophage activity level or the splenocyte activity level of the macrophages or of the splenocytes obtained from the non-human animal is measured and assessed, a screening method of a suppressor or a promoter of responsiveness to bacterial cell components characterized in comprising the steps of: the non-human animal being unresponsive to bacterial cell components is made to be infected with bacteria in advance; macrophages or splenocytes obtained from the non-human animal are cultured in the presence of a subject material; the macrophage activity level or the splenocyte activity level of the macrophages or of the splenocytes is measured and assessed, a screening method of a suppressor or a promoter of responsiveness to bacterial cell components characterized in comprising the steps of: the non-human animal being unresponsive to bacterial cell components is made to be infected with bacteria in advance; a subject material is administered to the non-human animal; the macrophage activity level or the splenocyte activity level of the macrophages or of the splenocytes obtained from the non-human animal is measured and assessed, a screening method of a suppressor or a promoter of responsiveness to bacterial cell components characterized in comprising the steps of: a subject material is administered in advance to the non-human animal being unresponsive to bacterial cell components; the non-human animal is made to be infected with bacteria; the macrophage activity level or the splenocyte activity level of the macrophages or of the splenocytes in the non-human animal is measured and assessed, a screening method of a suppressor or a promoter of responsiveness to bacterial cell components characterized in comprising the steps of: the non-human animal being unresponsive to bacterial cell components is made to be infected with bacteria in advance; a subject material is administered to the non-human animal; the macrophage activity level or the splenocyte activity level of the macrophages or of the splenocytes in the non-human animal is measured and assessed), the screening method of a suppressor or a promoter of responsiveness to bacterial cell components, wherein those levels are assessed in comparison to the measured value of a wild type non-human animal as control, which is the same species of the non-human animal being unresponsive to bacterial cell components, in the measurement and the assessment of the macrophage activity level or the splenocyte activity level, the screening method of a suppressor or a promoter of responsiveness to bacterial cell components, wherein the measurement and the assessment of the macrophage activity level is the measurement and the assessment of the production amount of cytokine and/or nitrous ion in the macrophage, the screening method of a suppressor or a promoter of responsiveness to bacterial cell components, wherein the measurement and the assessment of the splenocyte activity level is the measurement and the assessment of the expression amount of MHC class II in the splenocyte, the screening method of a suppressor or a promoter of responsiveness to bacterial cell components, wherein the bacterial cell component is a lipoprotein/lipopeptide, the screening method of a suppressor or a promoter of responsiveness to bacterial cell components, wherein the lipoprotein/lipopeptide is derived from cell components of bacteria which belong to *Mycoplasma, Spirochaeta, Escherichia* or the like, the screening method of a suppressor or a promoter of responsiveness to bacterial cell components, wherein the bacterial cell component is peptidoglycan, the screening method of a suppressor or a promoter of responsiveness to bacterial cell components, wherein the bacterial cell component is endotoxin, the screening method of a suppressor or a promoter of responsiveness to bacterial cell components, wherein the bacterial cell component is lipoteichoic acid, the screening method of a suppressor or a promoter of responsiveness to bacterial cell components, wherein the bacterial cell component is *Mycobacterium tuberculosis* lysate, the screening method of a suppressor or a promoter of responsiveness to bacterial cell components, wherein the suppressor or the promoter of responsiveness to bacterial cell components is a suppressor or a promoter of bacterial infection, the screening method of a suppressor or a promoter of responsiveness to bacterial cell components, wherein the suppressor or the promoter of responsiveness to bacterial cell components is an agonist or an antagonist of TLR2, the screening method of a suppressor or a promoter of responsiveness to bacterial cell components, wherein the suppressor or the promoter of responsiveness to bacterial cell components is a suppressor or a promoter of interleukin-1 activity, the screening method of a suppressor or a promoter of responsiveness to bacterial cell components, wherein the suppressor or the promoter of responsiveness to bacterial cell components is a suppressor or a promoter of interleukin-18 activity, the screening method of a suppressor or a promoter of responsiveness to bacterial cell components, wherein the suppressor or the promoter of responsiveness to bacterial cell components is a suppressor or a promoter of IFN-γ activity, and the screening method of a suppressor or a promoter of responsiveness to bacterial cell components, wherein the suppressor or the promoter of responsiveness to bacterial cell components is a suppressor or a promoter of TNF-α activity.

The present invention also relates to a suppressor or a promoter of responsiveness to bacterial cell components characterized in being obtainable by the screening method of a suppressor or a promoter of responsiveness to bacterial cell components, the suppressor or the promoter of responsiveness to bacterial cell components, wherein the suppressor or the promoter of responsiveness to bacterial cell components is a suppressor or a promoter of bacterial infection, and the suppressor or the promoter of responsiveness to bacterial cell components, wherein the suppressor or the promoter of responsiveness to bacterial cell components is an agonist or an antagonist of TLR2.

The present invention further relates to an assessing method of a subject material characterized in comprising the steps of: the subject material is administered to the non-human animal being unresponsive to bacterial cell components; the bioactivity of the subject material is assessed, an assessing method of a subject material characterized in comprising the steps of: the subject material is administered to the non-human animal being unresponsive to bacterial cell components, and to a wild-type non-human animal of the non-human animal respectively; the bioactivity of each subject material is compared and assessed, the assessing method of a subject material, wherein the bioactivity is an endotoxin activity, the assessing method of a subject material, wherein the bioactivity is an interleukin-1 activity, and the assessing method of a subject material, wherein the bioactivity is an interleukin-18 activity.

The present invention also relates to a method of detecting bacterial cell components characterized in comprising the steps of: a subject material is administered to the non-human animal being unresponsive to bacterial cell components; bacterial cell components in the subject material are detected, a method of detecting bacterial cell components characterized in comprising the steps of: the subject material is administered to the non-human animal being unresponsive to bacterial cell components and to a wild-type non-human animal of the non-human animal respectively; bacterial cell components in the subject materials are detected, the method of detecting bacterial cell components, wherein the bacterial cell component is a lipoprotein/lipopeptide, the method of detecting bacterial cell components, wherein the lipoprotein/lipopeptide is derived from cell components of bacteria which belong to *Mycoplasma, Spirochaeta* or *Escherichia*, the method of detecting bacterial cell components, wherein the bacterial cell component is peptidoglycan, the method of detecting bacterial cell components, wherein the bacterial cell component is endotoxin, and the method of detecting bacterial cell components, wherein the bacterial cell component is lipoteichoic acid.

The present invention further relates to a TLR2 knockout mouse characterized in being obtainable by a process comprising the steps of: a targeting vector is constructed by replacing a whole or a part of a gene fragment of an exon region containing a cytoplasmic region of TLR2 gene obtained by screening a mouse genomic library with a probe derived from a mouse EST clone with a plasmid having a poly A signal and a marker gene; the targeting vector is linearized and then introduced into an embryonic stem cell; chimeric mice are generated by microinjecting the targeting ES cells whose function of TLR2 gene is deficient into the blastocysts of mice; heterozygous mice are generated by mating the chimeric mice and wild-type mice; the heterozygous mice are interclossed, and an MyD88 knockout mouse characterized in being obtainable by a process comprising the steps of: a targeting vector is constructed by replacing a whole or a part of a gene fragment of two exon regions encoding a C-terminal portion of MyD88 gene region obtained by screening a mouse genomic library with a probe derived from a mouse EST clone with a plasmid having a poly A signal and a marker gene; the targeting vector is linearized and then introduced into the embryonic stem cell; chimeric mice are generated by microinjecting the targeting ES cells whose function of MyD88 gene is deficient into the blastocysts of mice; heterozygous mice are generated by mating the chimeric mice and wild-type mice; the heterozygous mice are intercrossed (claim 51).

BRIEF EXPLANATION OF DRAWINGS

FIG. 5 is a graph showing the results of NK cell activation mediated by IL-18 in the MyD88 knockout mice and the wild-type mice of the present invention.

BEST MODE FOR CARRYING OUT THE INVENTION

Figure 1:
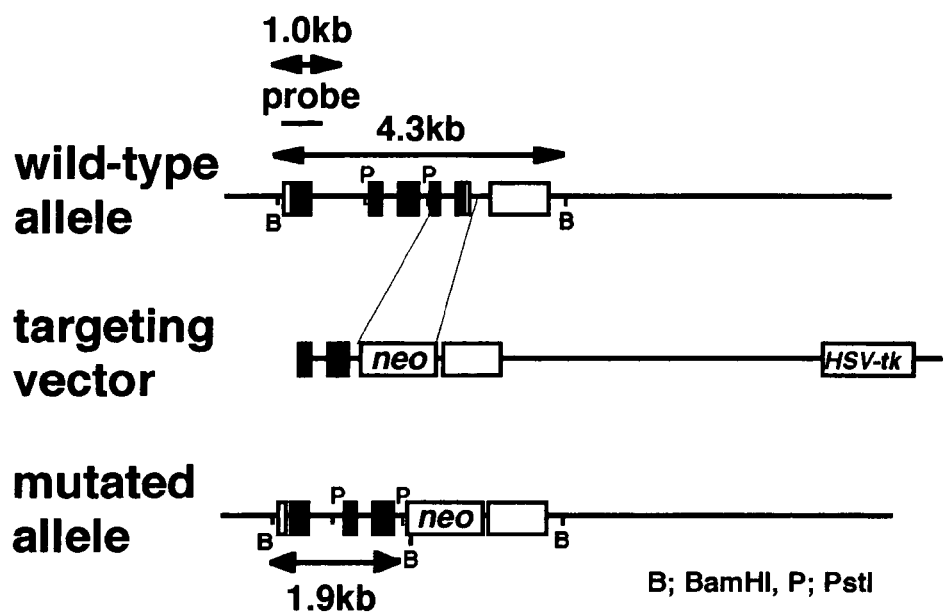
FIG. 1 is a graph showing gene maps of the MyD88 knockout mice and the wild-type mice of the present invention.

Examples of bacterial cell components of the present invention include: a lipoprotein/lipopeptide, which is a cell component of bacteria which belong to *Mycoplasma, Spirochaeta, Escherichia*; peptidoglycan comprised by combining repeating polysaccharides of N-acetylglucosamine and N-acetylmuramic acid, which is a skeletal structure of bacterial cell wall, and relatively short peptide chain; lipopolysaccharide (LPS) which exists mainly as an outer membrane component of Gram-negative bacteria and is also called endotoxin; lipoteichoic acid (LTA), which is a cell wall component of Gram-positive bacteria; *Mycobacterium tuberculosis* lysate; and a cell wall fraction of Gram-positive bacteria. Further, in the present invention, carriers which carry the above mentioned bacterial cell components, and the bacterial cell themselves are expediently included in the examples of the bacterial cell components.

In the present invention, "unresponsiveness to bacterial cell components" means that living organisms, or cells, tissue, or organs which comprise living organisms show low reactivity or almost no reactivity to the stimuli of the bacterial cell components, and "hyporesponsiveness" means low reactivity to the stimuli. Therefore, a model non-human animal being unresponsive to bacterial cell components in the present invention means a non-human animal such as a mouse, a rat, a rabbit or the like, where living organisms, or cells, tissue, or organs which comprise living organisms show low reactivity or almost no reactivity to the stimuli of the bacterial cell components. Examples of the stimuli of the bacterial cell components include an in vivo stimulus where a bacterial cell component is administered to a living organism and an in vitro stimulus where a bacterial cell component is brought into contact with cells separated from a living organism. As a example of a model non-human animal being unresponsive to bacterial cell components, a non-human animal unresponsive to bacterial cell components such as a lipoprotein/lipopeptide, peptidoglycan, a cell wall fraction of Gram-positive bacteria, endotoxin, lipoteichoic acid, *Mycobacterium tuberculosis* lysate and the like is exemplified, and specifically, a non-human animal whose function of TLR2 gene is deficient on its chromosome, such as a TLR2 knockout mouse and the like, and a non-human animal whose function of MyD88 gene is deficient on its chromosome, such as a MyD88 knockout mouse and the like are exemplified.

In the present invention, "deficiency of MyD88 or TLR2 gene function on a chromosome" means that a part of or a whole of MyD88 or TLR2 gene on a chromosome is deficient and the function to express MyD88 or TLR2, which is expressed in wild-types, is lost. Examples of a non-human animal whose function of MyD88 or TLR2 gene is deficient on its chromosome include a rodent such as a rat or the like whose function of MyD88 or TLR2 gene is deficient other than MyD88 or TLR2 knockout mice.

The term "a wild-type non-human animal" in the present invention means a non-human animal being the same species of the non-human animal whose function of MyD88 or TLR2 gene is deficient on its chromosome. For example, in case of mice, it means MyD88- or TLR2-nondeficient type mice of same species among F2 mice generated at the expected Mendelian ratio. When the deficient type and the wild-type mice of these F2 mice, in particular, the wild-type littermates are used for experiments simultaneously, it becomes possible to conduct precise comparative experiments at individual level. With an example of knockout mice which have deficiency in MyD88 or TLR2, a generating method of the non-human animal whose function of MyD88 or TLR2 gene is deficient on its chromosome will now be explained.

MyD88 or TLR2 gene can be cloned by amplifying a mouse genomic library by PCR or other methods with a probe derived from a mouse EST clone or the like. By DNA recombination technique, a part of or a whole of this cloned MyD88 or TLR2 gene, for example, a part or a whole of an exon region containing a cytoplasmic region of MyD88 or TLR2 gene are replaced with a poly A signal and a marker gene such as a neomycin resistance gene or the like, a targeting vector is constructed by inducing genes such as diphtheria toxin A fragment (DT-A) gene or herpes simplex virus thymidine kinase (HSV-tk) gene or the like into 5'-terminal side, this constructed targeting vector is linearized, and introduced into embryonic stem cells (ES cells) by electroporation method or the like, then cultured, and subsequently Es cells achieving homologous recombination by G418, ganciclovir (GANC) or other such antibiotics are selected. It is preferable to confirm whether these selected ES cells are the object recombinants by Southern blot analysis or the like.

Chimeric mice can be obtained by microinjecting the recombined ES cells into blastocysts of mice, and put the blastocysts back into uteri of recipient mice. Under high chimeric ratio, there will be born much more male chimeric mice than female ones. In such case, heterologous recombinant mice (+/−: F1) are generated by interclossing the chimeric mice with female wild-type mice, and the homologous recombinant mice [F2; wild-type mice (+/+), MyD88 or TLR2 knockout mice (−/−)] can be obtained by mating the heterologous recombinant male mice and female mice. All of these mice are generated at the expected Mendelian ratio. As the method of confirming whether MyD88 or TLR2 knockout mice of the present invention are born, for example, the method wherein RNA is isolated from peritoneal macrophages of mice obtained by the above-stated method, and is examined by Northern blot analysis or the like, and the method wherein the expression of MyD88 or TLR2 in the mice is examined by Western blot analysis or the like are exemplified.

It is possible to confirm that the generated MyD88 knockout mice are unresponsive to cell wall components of bacteria, for example, by contacting a lipoprotein/lipopeptide, which is a cell component of bacteria which belong to *Mycoplasma, Spirochaeta, Escherichia* or the like with macrophages of MyD88 knockout mice or human monocytes in vitro, and then measuring the production amount of TNF-α or $NO_2^-$ in the cells; by injecting LPS, which is a cell wall component of Gram-negative bacteria into MyD88 knockout mice by intravenous injection or the like, and then measuring bioactivity of endotoxin such as fever, shock, decrease of leukocytes or platelet, hemorrhagic necrosis of bone marrow cells, hypoglycemia, induction of IFN, activation of B limphocyte (immune response cell derived from marrow) or the like; by measuring the induction of IFN, proliferative response of splenic B cells, the expression of MHC class II antigen on the surface of splenic B cells, in macrophages or splenic B cells of MyD88 knockout mice, in the presence of LPS derived from bacteria, or peptidoglycan, which is a cell component of Gram-negative bacteria, lipotheichoic acid, *Mycobacterium tuberculosis* lysate or the like.

The MyD88 knockout mice of the present invention are unresponsive to a lipoprotein/lipopeptide, which is a bacterial cell component, and show lower responsiveness to endotoxin than C3H/HeJ mice, which have been known as being hyporesponsive to endotoxin so far, and no shock symptom has been observed. Moreover, macrophages and splenic B cells of MyD88 knockout mice are unresponsive not only to endotoxin but also to peptidoglycan being a cell wall component of Gram-positive bacteria, lipotheichoic acid, *Mycobacterium tuberculosis* lysate and the like, while they are responsive to IL-4 and IFN-γ. Therefore, the knockout mice being unresponsive to bacterial cell components can be used as useful model for elucidating action mechanisms of a lipoprotein/lipopeptide, endotoxin, peptidoglycan, lipotheichoic acid or the like, and for establishing a treatment method for endotoxin shock.

Further, the generated TLR2 knockout mice can be confirmed to be unresponsive to cell wall fractions of bacteria, for example, by contacting a lipoprotein/lipopeptide, which is a cell component of bacteria which belong to *Mycoplasma, Spirochaeta, Escherichia* or the like with macrophages of TLR2 knockout mice or human monocytes in vitro, and then measuring the production amount of TNF-α or $NO_2$ in the cells; by measuring the induction of TNF, proliferative response of splenocytes, the expression of MHC class II antigen on the surface of splenic B cells and the like, in macrophages or splenic B cells of TLR2 knockout mice, in the presence of cell wall fractions of Gram-positive bacteria, peptidoglycan, which is a cell wall component of Gram-positive bacteria or the like. The TLR2 knockout mice of the present invention are unresponsive to a lipoprotein/lipopeptide, which is a bacterial cell component, and peptidoglycan, and hyporesponsive to cell wall fractions of Gram-positive bacteria, and responsive to LPS, LTA and IL-4. Therefore, the TLR2 knockout mice can be used as useful model for elucidating action mechanisms of a lipoprotein/lipopeptide, peptidoglycan, cell wall fractions of Gram-positive bacteria or the like.

The non-human animals being unresponsive to bacterial cell components of the present invention can be used for screening of a suppressor or a promoter of bacterial infection, a suppressor or a promoter of responsiveness to bacterial cell components such as an agonist or an antagonist to TLR2, for assessment of bioactivity of various subject materials, for detection of bacterial cell components, and the like, other than for elucidating action mechanisms of bacterial cell components. A screening method of a suppressor or a promoter of bacterial infection or a suppressor or a promoter of responsiveness to bacterial cell components such as an agonist or an antagonist to TLR2 will be explained below with examples of the screening method of a suppressor or a promoter of bacterial infection.

Followings are exemplified as examples. The screening method of preventives and immune response restoratives/promoters and the like in bacterial infection comprising the steps of: macrophages, splenocytes or the like obtained from the non-human animal being unresponsive to bacterial cell components of the present invention and a subject material are brought into contact in advance in vitro; the macrophages or the splenocytes are cultured in the presence of bacterial cell components; the macrophage activity level or the splenocyte activity level of the macrophages or of the splenocytes is measured and assessed, and the screening method of remedies, symptom improvers and the like for bacterial infection comprising the steps of: macrophages or splenocytes obtained from the non-human animal being unresponsive to bacterial cell components of the present invention and bacterial cell components are brought into contact in advance in vitro; the macrophages or the splenocytes are cultured in the presence of a subject material; the macrophage activity level or the splenocyte activity level of the macrophages or of the splenocytes is measured and assessed.

In addition, the examples include the screening method of preventives and immune response restoratives/promoters and the like for bacterial infection comprising the steps of: a subject material is administered in advance to the non-human animal being unresponsive to bacterial cell components of the present invention; macrophages or splenocytes obtained from the non-human animal are cultured in the presence of bacterial cell components; the macrophage activity level or the splenocyte activity level of the macrophages or of the splenocytes is measured and assessed, and the screening method of preventives and immune response restoratives/promoters and the like for bacterial infection comprising the steps of: a subject material is administered in advance to the non-human animal being unresponsive to bacterial cell components of the present invention; the non-human animal is made to be infected with bacteria; the macrophage activity level or the splenocyte activity level of the macrophages or of the splenocytes obtained from the non-human animal is measured and assessed.

Further, the screening method of remedies, symptom improvers and the like for bacterial infection comprising the steps of: the non-human animal being unresponsive to bacterial cell components of the present invention is made to be infected with bacteria in advance; macrophages or splenocytes obtained from the non-human animal are cultured in the presence of a subject material; the macrophage activity level or the splenocyte activity level of the macrophages or of the splenocytes is measured and assessed, and the screening method of remedies, symptom improvers and the like for bacterial infection comprising the steps of: the non-human animal being unresponsive to bacterial cell components of the present invention is made to be infected with bacteria in advance; a subject material is administered to the non-human animal; the macrophage activity level or the splenocyte activity level of the macrophages or of the splenocytes obtained from the non-human animal is measured and assessed are exemplified.

Furthermore, the screening method of preventives and immune response restoratives/promoters and the like for bacterial infection comprising the steps of: a subject material is administered in advance to the non-human animal being unresponsive to bacterial cell components of the present invention; the non-human animal is made to be infected with bacteria; the macrophage activity level or the splenocyte activity level in the non-human animal is measured and assessed, and the screening method of remedies, symptom improvers and the like for bacterial infection comprising the steps of: the non-human animal being unresponsive to bacterial cell components of the present invention is made to be infected with bacteria in advance; a subject material is administered to the non-human animal; the macrophage activity level or the splenocyte activity level in the non-human animal is measured and assessed are exemplified.

As a method of measuring and assessing the macrophage activity level, the method of measuring and assessing the production amount of cytokine and/or nitrous ion in the macrophage is exemplified, and as a method of measuring and assessing the splenocyte activity level, a method of measuring and assessing the expression amount of MHC class II in the splenocyte is exemplified. In the measurement and the assessment of the macrophage activity level or the splenocyte activity level, it is preferable to assess the levels in comparison to the measured value of a wild type non-human animal, in particular, a littermate wild type non-human animal of the non-human animal being unresponsive to bacterial cell components as control, because there will be no dispersion caused by individual differences. This can be applied to the assessment of bioactivity of various subject materials and detection of bacterial cell components and the like, in which the non-human animal being unresponsive to bacterial cell components of the present invention is used.

Examples of a suppressor or a promoter, which is the object of the screening methods of the present invention, include a suppressor or a promoter of responsiveness to bacterial cell components such as a lipoprotein/lipopeptide derived from a cell component of bacteria which belong to *Mycoplasma, Spirochaeta* or *Escherichia*, peptidoglycan, endotoxin, lipoteichoic acid, *Mycobacterium tuberculosis* lysate and the like, and a suppressor or a promoter of interleukin-1 activity, interleukin-18 activity, IFN-γ activity, TNF-α activity and the like, other than the suppressor or the promoter of bacterial infection, or the agonist or the antagonist to TLR2.

Though the screening of an agonist or an antagonist to TLR2 can be performed in the same manner as the screening of the suppressor or the promoter of bacterial infection as aforementioned, it is also possible to use TLR4 knockout mice together. In other words, it is possible to conduct the screening of the agonist or the antagonist to TLR2 and/or TLR4 by administering a subject material to each of TLR2 and TLR4 knockout mice, and to wild-type mice if necessary, and by comparing and assessing the activity levels of macrophages or splenocytes derived from the TLR2 knockout mice and the TLR4 knockout mice.

The assessing method of a subject material of the present invention is characterized by that the subject material is administered to the non-human animal being unresponsive to bacterial cell components of the present invention and then the bioactivity of the subject material is assessed. The bioactivity of the subject material, for example, endotoxin activity, interleukin-1 activity, interleukin-18 activity and the like can be assessed by the assessing method of the subject materials of the present invention. For instance, by precisely assessing endotoxin activity of a subject material with MyD88 knockout mice of the present invention, it becomes possible to obtain useful information for developing antagonists to endotoxin or other such pharmaceuticals which can suppress the shock or fever caused by endotoxin.

The relationship between IL-1 and the illness in disease model mice can be examined by precisely assessing IL-1 activity of a subject material with MyD88 knockout mice of the present invention. It becomes possible to obtain useful information for developing pharmaceuticals which can cure diseases such as rheumatoid arthritis caused by overexpression of IL-1, a graft-versus-host disease, asthma and the like by precisely assessing IL-1 activity of a subject material and by analyzing the involvement of IL-1 in disease model mice. Examples of IL-1 activity as an object of assessment include mitogens such as phytohemagglutinin (PHA), concanavalin A (Con A) and the like, proliferation inducing activity of T cells caused by co-stimulation with IL-2 at a low concentration, and activity which induces the production of TNF-α, IL-1 and IL-6 by working on monocytes and macrophages.

Moreover, by precisely assessing IL-1 activity of a subject material with MyD88 knockout mice of the present invention, it becomes possible to obtain useful information for developing pharmaceuticals which can cure diseases caused by overproduction of IL-18, such as I type diabetes, a graft-versus-host disease and the like. Examples of IL-18 activity as an object of assessment include activity which promotes production of IFN-γ, activity which enhances activity of NK cells, activity which induces production of IFN-γ from T cells in cooperation with IL-12, and action which activates IRAK or NF-$_κ$B.

With the method of detecting the bacterial cell components of the present invention, it is possible to detect insubstantial amount of bacterial cell components contained in subject materials in the non-human animal being unresponsive to bacterial cell components of the present invention after the subject material has been administered to the non-human animal. The examples of such bacterial cell components include; a lipoprotein/lipopeptide derived from a cell component of bacteria which belong to *Mycoplasma, Spirochaeta, Escherichia* and the like; endotoxin derived from *Escherichia coli, Klebsiella pneumoniae, Pseudomonas aeruginosa, Salmonella typhimurium, Serratia marcescens, Shigella flexneri, Vibrio cholerae, Salmonella minnesota, Porphyromonas gingivalis* and the like; peptidoglycan derived from *Staphylococcus aureus, Corynebacterium diphtheriae, Nocardia coeliaca* and the like; lipoteichoic acid derived from *Streptococcus pneumoniae* and the like; and whole cell lysates of *Mycobacterium tuberculosis*.

The present invention will be explained more specifically with examples below, but the technological scope of the present invention is not limited to these examples.

EXAMPLE 1

Generation of MyD88 Knockout Mice

A MyD88 gene was screened from a 129/SvJ mouse genomic library (Stratagene), subcloned into pBluescript vector (Stratagene), and characterized by restriction enzyme mapping and DNA sequencing. A targeting vector was constructed by replacing the 1.0 kb genomic fragment of the wild-type allele with a neomycin resistance gene from pMC1-neo (Stratagene). The replaced genomic fragment contained 2 exons encoding the domain that resembles the cytoplasmic domain of the IL-1RAcP (receptor accessory protein). The neomycin resistance gene was flanked by the 1.1 kb 5' genomic fragment and the 5.2 kb 3' fragment. Then, an HSV-tk cassette was introduced into the 3' end of the genomic fragment. E14.1 ES cells were transfected with the linearized targeting vector and selected with G418 and gancyclovir. Doubly resistant 176 clones were screened for homologous recombination by PCR and 33 clones were verified by Southern blot analysis using the probe indicated in FIG. 1.

Three independently identified targeted ES clones were microinjected into the blastocysts of C57BL/6 mice. Thus obtained chimeric mice were mated with C57BL/6 female mice to produce heterozygous mice. The Heterozygous mice were intercrossed to obtain homozygotes, and MyD88-deficient were born at the expected Mendelian ratios (+/+:+/−:−/−=52:93:53) from the intercross. The MyD88 knockout mice of the present invention grew healthy and showed no obvious abnormalities until 20 weeks of age. Northern blot analysis was performed to confirm that the inactivation of the MyD88 gene was caused by mutation. MyD88 mRNA could not be detected in the liver and the spleen of the MyD88-deficient mice. Flow cytometric analysis of CD3, B220, CD4, and CD8 in thymus, spleen, and lymph node showed that lymphocyte composition was not altered in the MyD88 knockout mice in comparison with wild-type mice.

EXAMPLE 2

Figure 2:
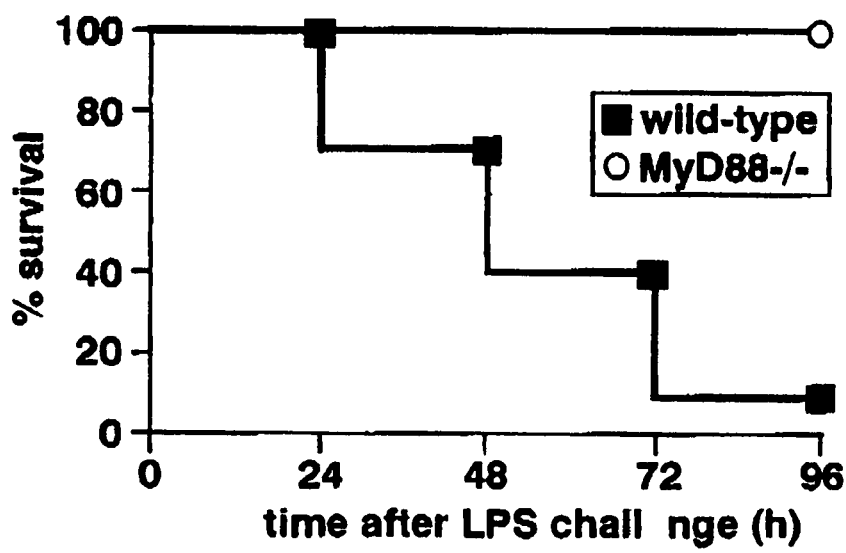
FIG. 2 is a graph showing survival indices of the MyD88 knockout mice and the wild-type mice of the present invention having an injection of LPS derived from *Escherichia coli*.

Unresponsiveness of MyD88 Knockout Mice to Endotoxin 1 mg of LPS derived from *Escherichia coli* (055:B5) was administered to 10 MyD88 knockout mice of the present invention, and endotoxin-unresponsiveness was examined through the survival ratio of the mice. 10 wild-type littermates were used as control. The results are shown in FIG. 2. It is confirmed by FIG. 2 that though the wild-type mice have responded to LPS and all of them died within 4 days after administration, none of the MyD88 knockout mice of the present invention have died within 4 days after LPS administration, and that the mice are endotoxin-unresponsive.

EXAMPLE 3

Figure 3:
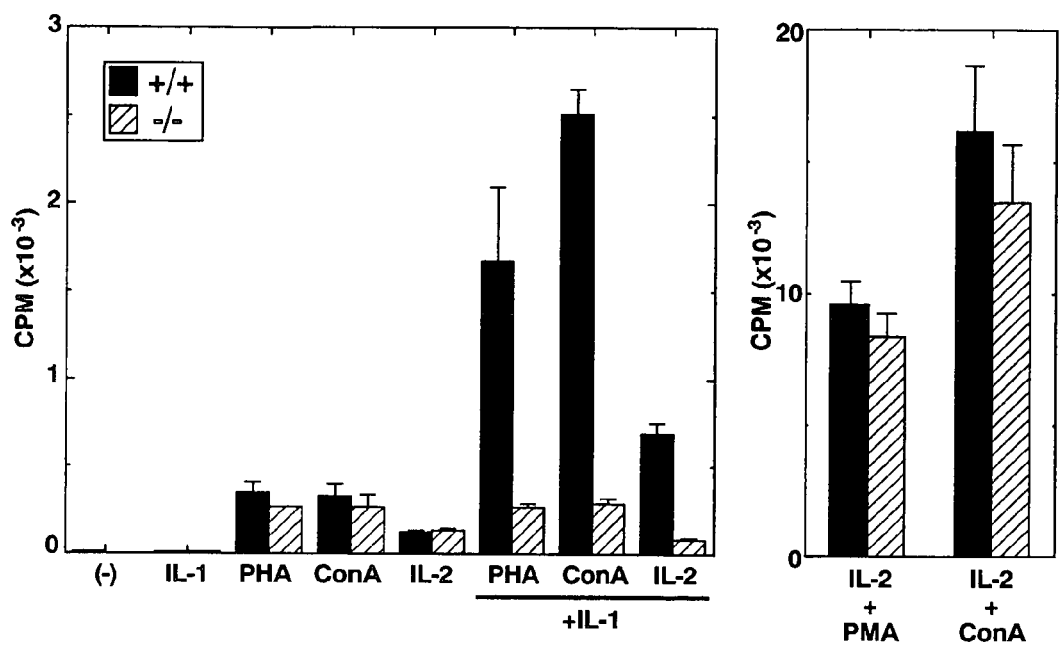
FIG. 3 is a graph showing the results of T cell proliferation mediated by IL-1 in the MyD88 knockout mice and the wild-type mice of the present invention.

Impaired IL-1-Mediated Functions in MyD88 Knockout Mice $1 \times 10^5$ of thymocytes of the MyD88 knockout mice of the present invention were cultured in 96-well plates for 72 hours with mixtures containing 2 μg/ml of phytohemagglutinin (PHA), which is a costimulant of IL-1 for T cell proliferation, 2.5 μg/ml of concanavalin A (ConA), or 2 ng/ml of IL-2 respectively, and 100 U/ml of IL-1β (Genzyme), and T cells were proliferated. Proliferation of T cells were examined by measuring [$^3$H] amount of [$^3$H] thymidine taken into the cells. As a result, thymocytes of wild-type littermates displayed enhanced proliferation when cultured with PHA, ConA or IL-2 in the presence of IL-β, however, thymocytes of the MyD88 knockout mice of the present invention show almost no enhanced proliferation (see FIG. 3). It has been found that similar results could be obtained even when splenic B cells were used instead of thymocytes.

Further, thymocytes of MyD88 knockout mice of the present invention were cultured with 10 ng/ml of phorbol 12-myristate 13-acetate paramethoxyamphetamine (PMA) or 2.5 μg/ml of Con A in the presence of 20 ng/ml of IL-2 (Genzyme) in a same manner as above-mentioned, and enhancement of proliferation was examined. There was no difference between thymocytes of MyD88 knockout mice of the present invention and of wild-type littermates in their proliferation as to the reaction of IL-2 and PMA or Con A (see FIG. 3). These results indicate that IL-1-mediated growth signal of T cells was impaired in the thymocytes of MyD88 knockout mice of the present invention.

MyD88 knockout mice of the present invention were intravenously injected with 1 μg of IL-β (Genzyme), and 2 hours later liver and sera were taken. Total RNA was extracted from the liver using Trizol reagent (GIBCO). This RNA (10 μg) was electrophoresed and transferred to a nylon membrane, then Northern blot analysis was conducted with $^{32}$P-labelled cDNA for acute phase proteins such as serum amyloid A (SAA-I), serum amyloid P(SAP), and haptoglobin (HP). In comparing IL-1-induced increase of mRNA expression in wild-type littermates and in MyD88 knockout mice of the present invention, increase of induction was observed in wild-type mice, but not observed in MyD88 knockout mice.

Figure 4:
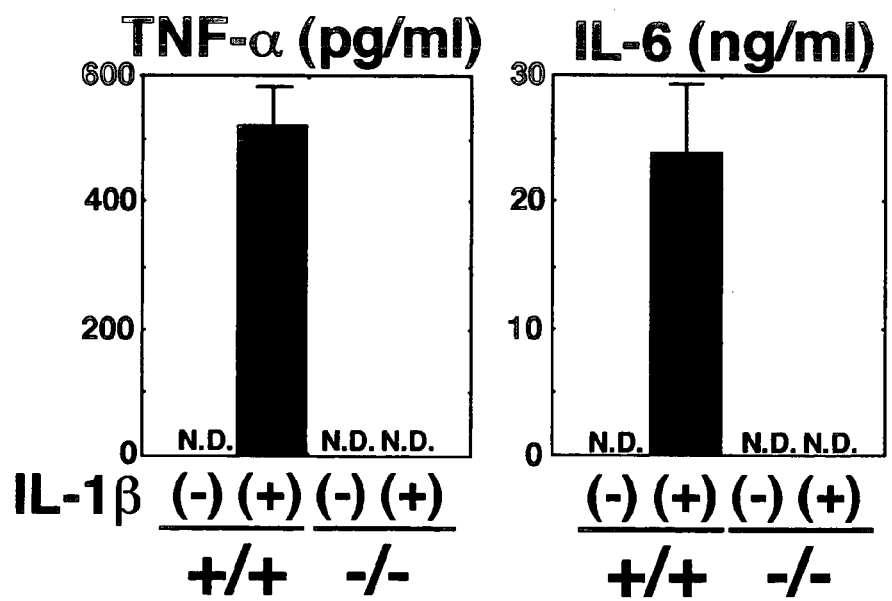
FIG. 4 is a graph showing the results of IL-1-induced TNF-α and IL-6 levels in blood in the MyD88 knockout mice and the wild-type mice of the present invention.

Because IL-1 induces production of acute phase proteins such as tumor necrosis factor (TNF-α) or IL-6, and proinflammatory cytokines, increase of TNF-α and IL-6 concentrations in serum taken from MyD88 knockout mice of the present invention and wild-type littermates by the above-stated method were measured by ELISA. As a result, TNF-α and IL-6 concentrations increased by IL-1β in wild-type mice, while neither TNF-α nor IL-6 concentration increased by IL-1β in MyD88 knockout mice (see FIG. 4).

Thus, IL-1-mediated major biological functions has been found to be severely impaired in MyD88 knockout mice of the present invention.

EXAMPLE 4

Impaired IL-18-Mediated Functions in MyD88 Knockout Mice

It has been well known that IL-18 enhances lytic activity of NK cells. Splenic B cells from MyD88 knockout mice of the present invention and wild-type littermates were cultured in the presence or absence of 20 ng/ml of IL-18 (Hayashibara Biochemical Laboratories, Inc.) for 24 hours with $^{51}$Cr-labelled mouse lymphoma cells (hereinafter "YAC-1") targeting cells. 4 hours later, released $^{51}$Cr in supernatants were counted by a gamma counter. As a result, when splenic B cells were cultured in the presence of IL-18 in vitro, lytic activity to YAC-1 targeting cells was dramatically enhanced in wild-type mice, but it was not enhanced in MyD88 knockout mice. When IL-2 was used instead of IL-18, lytic activity was also enhanced in splenic B cells of MyD88 knockout mice of the present invention (see FIG. 5).

Further, splenic B cells of MyD88 knockout mice of the present invention and their wild-type littermates were stimulated by 20 ng/ml of IL-18 and cultured for 24 hours in vitro, then production of IFN-γ in culture supernatants was measured by ELISA. As a result, production of IFN-γ was induced in wild-type mice, however, production of IFN-γ was not observed in MyD88 knockout mice of the present invention (see FIG. 5).

Figure 6:
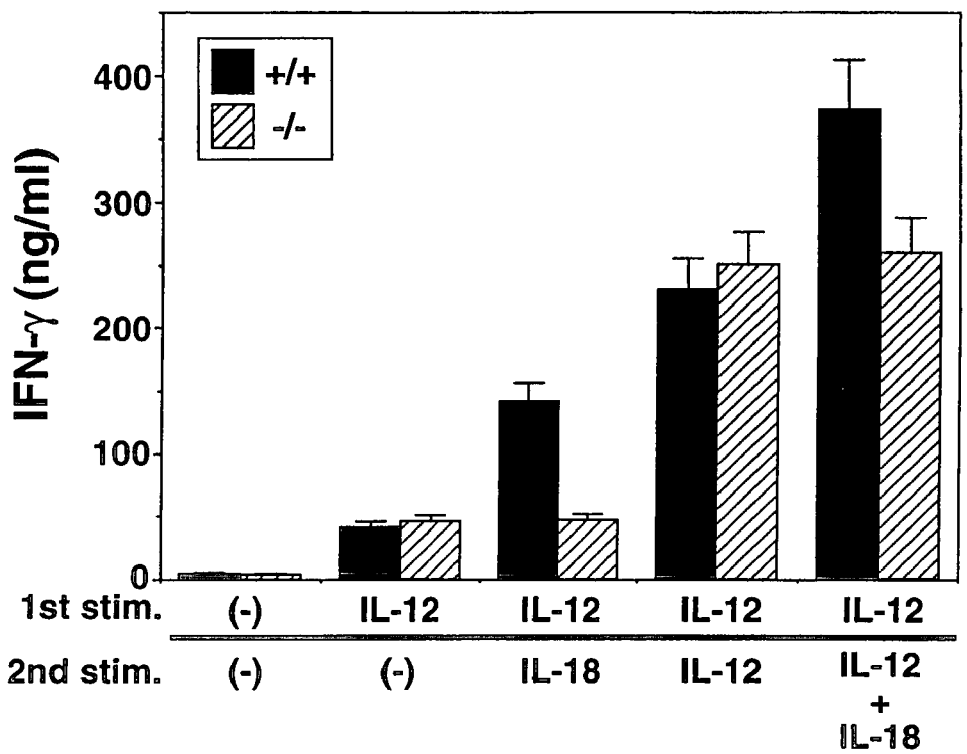
FIG. 6 is a graph showing the results of the production of IFN-γ stimulated by IL-12 and IL-18 in the MyD88 knockout mice and the wild-type mice of the present invention.
Figure 6:
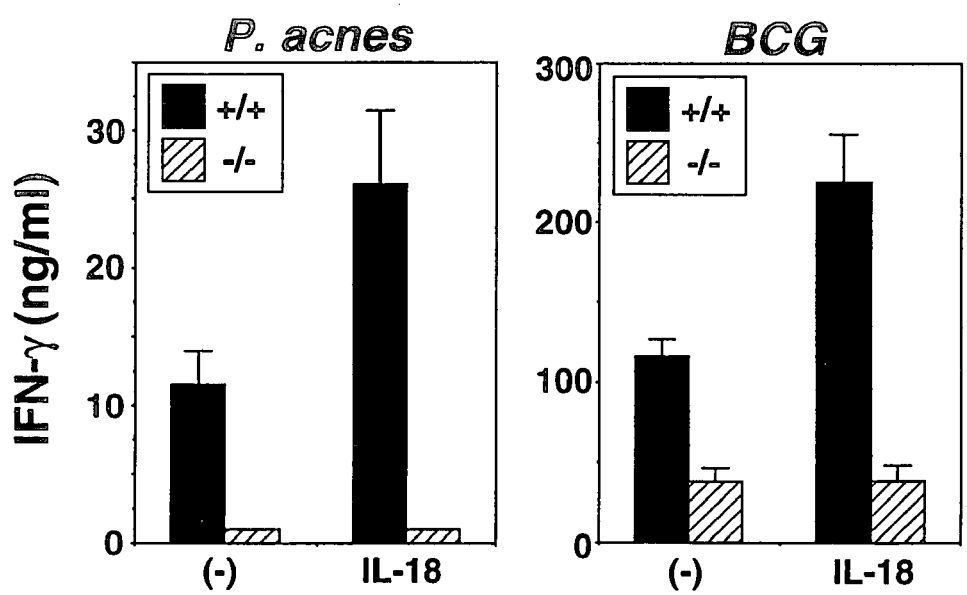

Splenic T cells of MyD88 knockout mice of the present invention and their wild-type littermates, which were purified to 95% or over, were cultured on anti-CD3 antibody (20 μg/ml)(PharMingen)-coated plates in the presence of 2 ng/ml IL-12. 4 days after the onset of culture, cells were harvested and washed with Hanks' balanced salt solution. The washed cells ($2 \times 10^5$) were stimulated and cultured again on anti-CD3 antibody (20 μg/ml)-coated 96-well plates for 24 hours with 20 ng/ml of IL-18 or 2 ng/ml of IL-12. Concentration of IFNγ in culture supernatants was determined by ELISA and compared. The result indicates that Splenic T cells of MyD88 knockout mice of the present invention cannot enhance IL-18-responsive production of IFNγ (see FIG. 6).

MyD88 knockout mice of the present invention and their wild-type littermates were intraperitoneally injected with 500 μg of heat-killed Propionibacterium acnes (P. acnes). Seven days after injection, T cells were purified from spleen, then cultured and stimulated on anti-CD3 antibody (20 μg/ml)-coated 96-well plates for 24 hours in the presence or the absence of 20 ng/ml of IL-18. Concentration of IFN-γ in culture supernatants was determined by ELISA. MyD88 knockout mice of the present invention and their wild-type littermates were intravenously injected with 2 mg of Bacillus Calmette-Guérin (BCG) (Kyowa). 14 days after injection, T cells were purified from spleen, then cultured and stimulated for 24 hours, as described above, subsequently concentration of IFN-γ was measured. As a result, in both cases, high level of IFN-γ production in response to IL-18 was observed in wild-type mice, but production level of IFN-γ could not be enhanced in the presence of IL-18 in MyD88 knockout mice of the present invention (see FIG. 6).

These results demonstrate that MyD88 knockout mice of the present invention are defective in Th1 cell development in vivo as is the case with IL-18-deficient mice, and that their major biological activities mediated by IL-18 were completely abolished.

Figure 7:
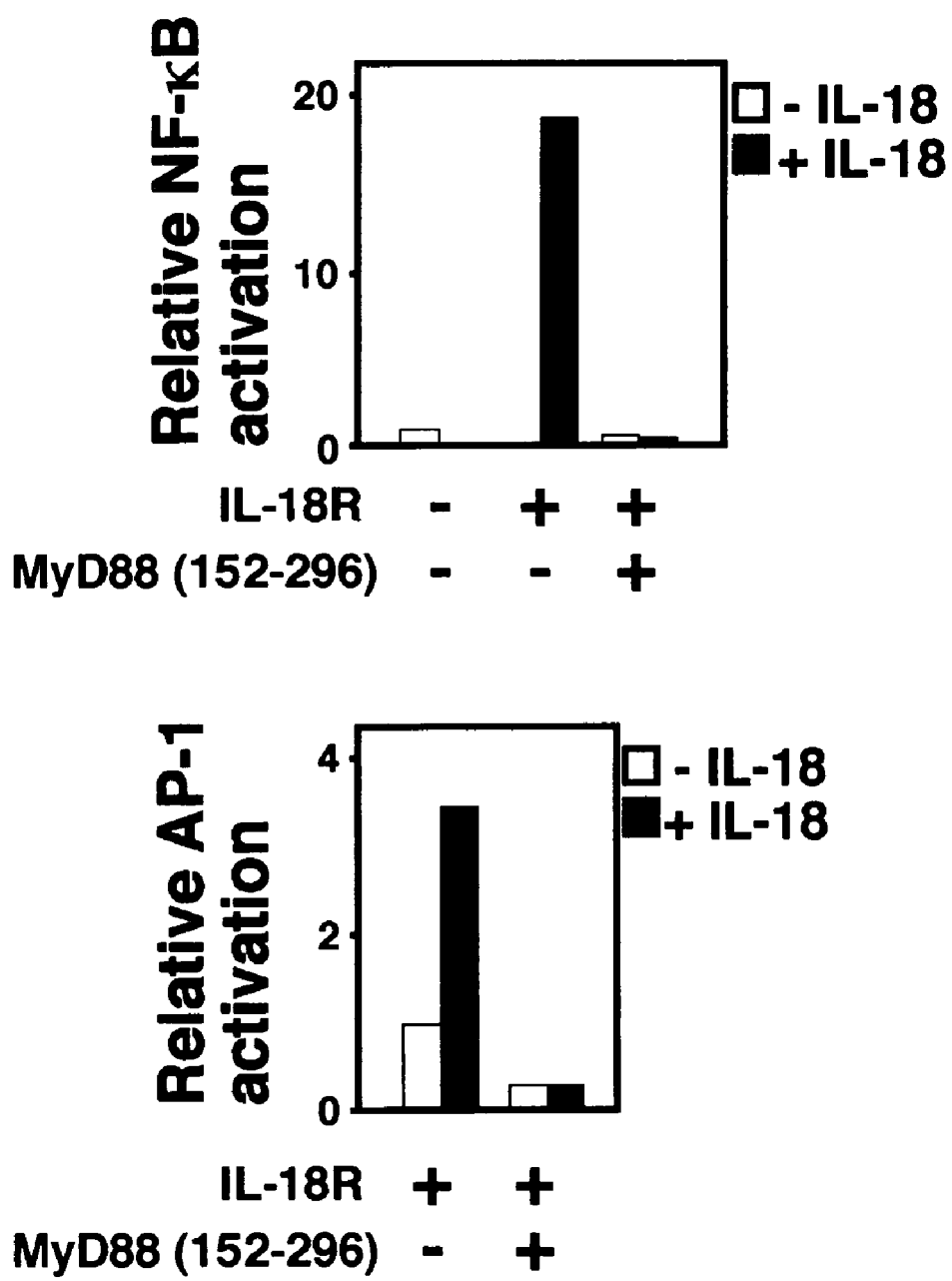
FIG. 7 is a graph showing that the mutation of dominant negative MyD88 is involved in IL-18-induced NF-$_κ$B activity and AP-1 activity.

Next, it was examined whether the dominant negative MyD88 mutant blocked IL-18-induced NF-$_κ$B activation as well. COS-7 cells were transiently transfected with MyD88 (amino acid 152–296) expression vector together with NF-$_κ$B-dependent luciferase reporter gene, and luciferase activity after IL-18 treatment was measured. Coexpression of MyD88 blocked IL-18-induced activation almost completely (see FIG. 7).

Because IL-18 activates AP-1-dependent gene information, whether MyD88 (amino acid 152–296) also acted as a dominant negative mutant of IL-18-induced AP-1 activation was investigated. Stimulation with IL-18-induced an approximately 3- to 4-fold increase in AP-1 activity, and this activation was blocked by coexpression of MyD88 (amino acid 152–296) (see FIG. 7). These results show that MyD88 is involved in IL-18-induced activation of both NF-$_κ$B and AP-1.

Further, whether IL-18-induced activation of NF-$_κ$B was observed in MyD88-deficient cells was examined. Splenic T cells cultured in the presence of IL-12 and anti-CD3 antibody for 4 days were starved for 3 hours and then stimulated with IL-18. Nuclei extracted from the stimulated cells were analyzed by a gel mobility shift assay using a specific probe containing NF-$_κ$B binding site. IL-18-induced NF-$_κ$B DNA binding activity was detected in the nuclear extracts from wild-type cells but not from MyD88-deficient cells. On the other hand, treatment of wild-type or MyD88-deficient thymocytes with TNF-α resulted in almost the same levels of NF-$_κ$B DNA binding activity, demonstrating that the impaired IL-18-induced NF-$_κ$B activity in MyD88-deficient cells was not due to the abnormal function or impairment of regulating ability of NF-$_κ$B.

In addition to induction of NF-$_κ$B activation, IL-1 is also known to activate c-Jun N-terminal kinase (JNK). To test whether IL-18 induces JNK activation, an in vitro kinase assay was carried out using GST-c-Jun-fusion protein as a substrate. Treatment with IL-18 induced JNK activation in Th1-developing cells of wild-type mice. However, IL-18-induced JNK activation was not observed in MyD88-deficient cells. By contrast, normal activation of JNK was observed in MyD88-deficient cells treated with TNF-α. IL-18-induced NF-$_κ$B and JNK activation was impaired in MyD88-deficient mice. These results demonstrate that MyD88 is essential for IL-18-induced activation of both NF-$_κ$B and JNK.

EXAMPLE 5

Unresponsiveness of Macrophages and Splenic B Cells of MyD88 Knockout Mice to Bacterial Cell Wall Components 5-1 (Generation of TLR4-Deficienct Mice)

It has recently been reported that C3H/HeJ mice are hyporesponsive to LPS because of a missense point mutation in the Toll-like receptor(TLR)-4 gene (Science 282, 2085–8, 1998, J. Exp. Med. 189, 615–625, 1999, J. Immunol. 162, 3749–3752, 1999), and the inventors have demonstrated that macrophages and splenic B cells of TLR4-deficient mice are hyporesponsive to LPS, and that TLR4 gene is essential for LPS signaling (J. Immunol. 162, 3749–3752, 1999). In order to compare the responsiveness of macrophages and splenic B cells of TLR4- and MyD88-deficient mice to bacterial cell wall components, TLR4-deficient mice ($F_2$ interbred from 129/O1aXC57BL/6) were generated by gene targeting as described previously (J. Immunol. 162, 3749–3752, 1999). Age-matched groups of wild-type, TLR4-, and MyD88-deficient mice were used for the following examples.

5-2 (Preparation of Bacterial Cell Wall Components)

LPS of *Escherichia coli* Serotype 055:B5 (Sigma), *Klebsiella pneumoniae* (Sigma), *Pseudomonas aeruginosa* Serotype 10 (Sigma), *Salmonella typhimurium* (Sigma), *Serratia marcescens* (Sigma), *Shigella flexneri* Serotype 1A (Sigma) and *Vibrio cholerae* Serotype Inaba 569B (Sigma) and the like were purchased. They were prepared by phenol extraction and purified by gel filtration. LPS from *Salmonella minnesota* Re-595 prepared by phenol-chloroform-petroleum ether extraction procedure was also purchased (Sigma). LPS and Lipid A of *Porphyromonas gingivalis* 381 was prepared by the method as describedpreviously (FEBS Lett. 332, 1994, 197–201). Whole cell lysates of *Mycobacterium tuberculosis* was prepared by the following process: *Mycobacterium tuberculosis* Aoyama B strain (NIHJ 1635) was cultured in Dubos broth (DIFCO) for 1 month; cells were collected and resuspended with phosphate buffered saline (PBS); cells were sonicated.

5-3 (Preparation of Peritoneal Macrophages)

2 ml of 4% thioglycollate was intraperitoneally injected into the generated wild-type, TLR4- and MyD88-deficient mice respectively. Three days later, peritoneal exudate cells were isolated from the peritoneal cavity and washed with ice-cold Hank's buffered salt solution (HBSS), then peritoneal cells were obtained. The cells were made to float in RPMI 1640 medium, then put in plastic plates separatedly, and cultured for 2 hours at 37° C. and washed with Hank's buffered salt solution to remove nonadherent cells. Adherent cells were used as peritoneal macrophages in the experiments bellow.

5-4 (Unresponsiveness to LPS of *Salmonella minnesota* Re-595)

Figure 8:
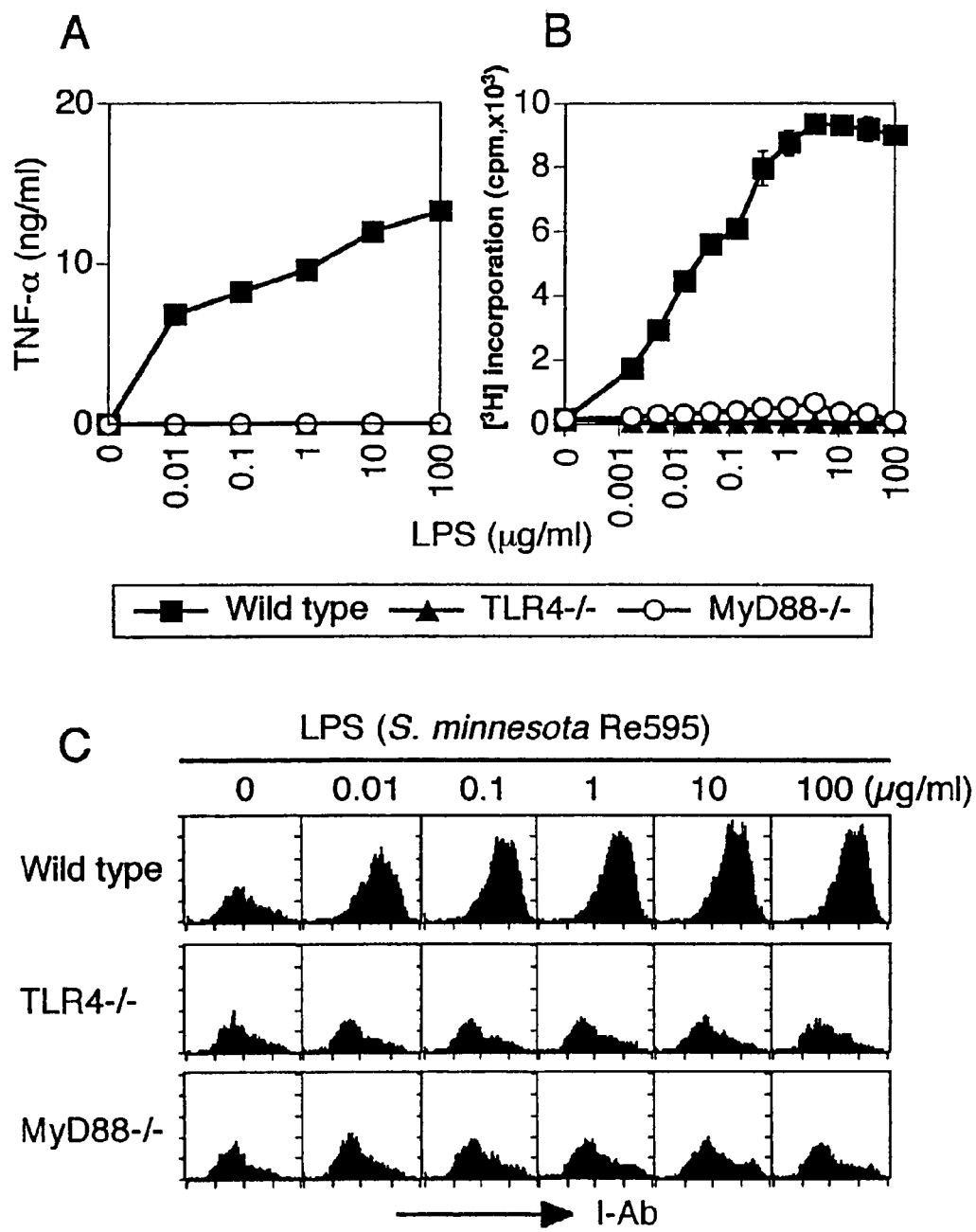
FIG. 8(A–C) is a graph showing the results of responsiveness of macrophages and splenic B cells of the MyD88 knockout mice, the wild-type mice and the TLR4 knockout mice of the present invention to *Salmonella minnesota* Re-595.

Responsiveness of each peritoneal macrophage of the wild-type (wild-type), TLR4-deficient (TLR4−/−), MyD88-deficient (MyD88−/−) mice and the like to LPS were examined with LPS of *Salmonella minnesota* Re-595. Peritoneal macrophages from each mouse were cultured for 24 hours in the presence of various concentrations (0, 0.01, 0.1, 1, 10 or 100 μg/ml) of LPS and stimulated, then concentration of tumor necrosis factor (TNF-α) released from LPS-responsive macrophages was measured by ELISA (see FIG. 8A). By these results, it has been found that production of TNF-α increases in response to LPS in a dose-dependent manner in macrophages of wild-type mice, by contrast, no production of TNF-α is observed in TLR4- or MyD88-deficient mice even when they receive LPS stimuli at a concentration of 100 μg/ml, and that these mice are LPS-unresponsive.

Further, responsiveness of splenic B cells to LPS of *Salmonella minnesota* Re-595 was examined. Splenic B cells ($1 \times 10^5$) of each of the wild-type, TLR4- and MyD88-deficient mice were isolated, cultured in 96-well plates and stimulated by various concentrations (0, 0.01, 0.1, 1, 10 or 100 μg/ml) of LPS. 1 μCi of [$^3$H]-thymidine (DuPont) was added 40 hours after onset of the culture, then the cells were cultured for another 8 hours, and [$^3$H] uptake was measured by a β scintillation counter (Packard) (see FIG. 8B). As a result, LPS-induced proliferative response was promoted in response to LPS in a dose-dependent manner in splenic B cells of wild-type mice, by contrast, no LPS-induced proliferative response was observed in splenic B cells of both TLR4- and MyD88-deficient mice.

The expression of major histocompatibility complex (MHC) class II (I-A$^b$ molecule) on the surface of splenic B cells in response to Re-595LPS was examined by flow cytometry. Splenic B cells ($1 \times 10^6$) from each of the wild-type, MyD88- and TLR4-deficient mice were cultured for 48 hours in the presence of various concentrations (0, 0.01, 0.1, 1, 10 or 100 μg/ml) of LPS. After the culture, the cells were collected and then stained by combining I-A$^b$ molecule on the surface of the cells and FITC-labelled antibody which is constructed by combining phycoerythrin (PE; PharMingen)-conjugated anti-B220 antibody or biotinylated anti-mouse I-A$^b$ antibody (PharMingen) and fluorescein isocyanate (FITC; PharMingen)-conjugated streptavidin. The stained cells were analyzed on fluorescence-activated cell sorter Calibur (FACS Calibur) using CELLQuest software (Becton Dickinson). As a result, Re-595 LPS caused an increase in the expression of I-A$^b$ molecule on the surface of splenic B cells of wild-type mice. In contrast, Re-595 LPS did not enhance I-A$^b$ molecule expression in splenic B cells of either TLR4- or MyD88-deficient mice, even when stimulated with high concentration of LPS (100 μg/ml) (see FIG. 8C). The above-mentioned results indicate that both TLR4- and MyD88-deficient mice are unresponsive to LPS of *Salmonella minnesota* Re-595.

5-5 (Responsiveness of TLR4- and MyD88-deficient mice to IL-4 and IFN-γ)

In order to examine whether splenic B cells of TLR4- and MyD88-deficient mice are unresponsive to all stimuli, the responsiveness of splenic B cells of TLR4- and MyD88-deficient mice to other stimuli were investigated. The investigation demonstrates that there was no impairment as to their responsiveness to the stimuli as described below, and that these mice were specifically defective in their response to LPS.

Figure 9:
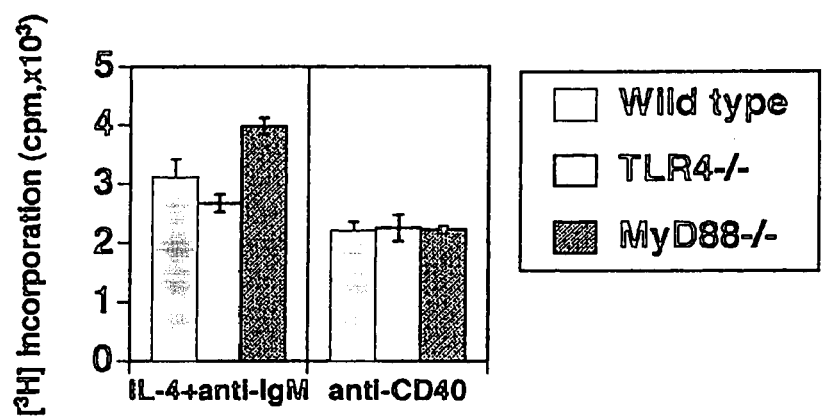
FIG. 9(A–C) is a graph showing the results of responsiveness of macrophages and splenic B cells of the MyD88 knockout mice, the wild-type mice and the TLR4 knockout mice of the present invention to IL-4 and interferon-γ.
Figure 9:
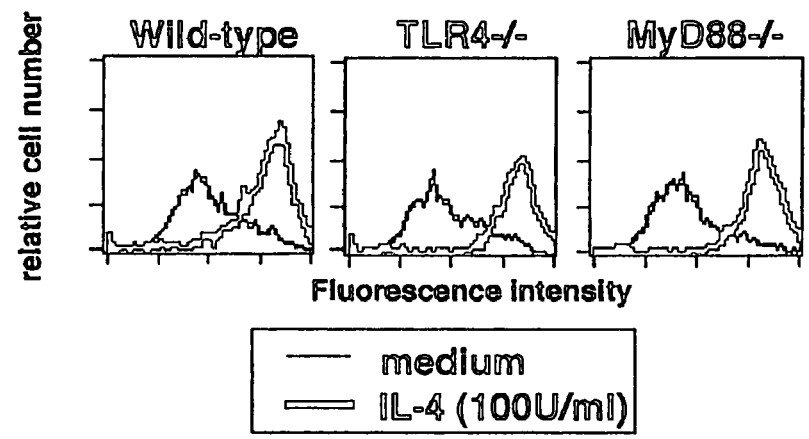
Figure 9:
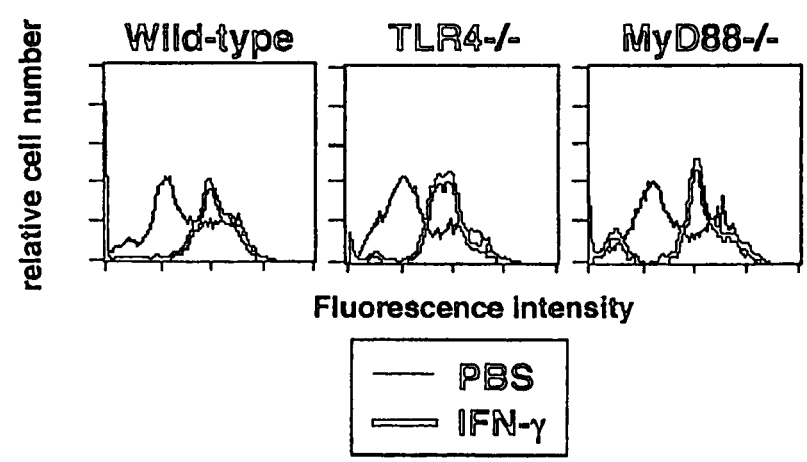

Splenic B cells (1×10⁵) from each of the wild-type, MyD88- and TLR4-deficient mice were isolated, cultured for 40 hours in the presence of both IL-4 (Genzyme) and anti-IgM antibody, or in the presence of anti-CD40 antibody, then [$^3$H]-thymidine (DuPont) was added and the cells were cultured for another 8 hours, and [$^3$H] uptake was measured by a β scintillation counter (see FIG. 9A). As a result, splenic B cells of both TLR4- and MyD88-deficient mice showed same reaction as splenic B cells of wild-type mice with regard to the response to IL-4 and the mixture of anti-IgM antibody, or to the anti-CD40 antibody.

Next, Splenic B cells (1×10⁶) from each of the wild-type, MyD88- and TLR4-deficient mice were cultured for 48 hours in the presence or absence of 100 U/ml of IL-4, and then stimulated. Subsequently, the cells were stained by combining I-A$^b$ molecule on the surface of the splenic B cells and PE-conjugated anti-B220 antibody or FITC-conjugated anti-mouse I-A$^b$ antibody. The cell proliferation was measured on fluorescence-activated cell sorter Calibur using CELLQuest software (see FIG. 9B). As a result, splenic B cells of both TLR4- and MyD88-deficient mice showed same reaction as those of wild-type mice with regard to the response to IL-4 as well.

Each of wild-type, MyD88- and TLR4-deficient mice were intraperitoneally injected with 5000 U of IFN-γ (Genzyme) or PBS. Three days after injection, peritoneal macrophages were collected and stained by combining I-A$^b$ molecule on the surface of the macrophage membranes and FITC-conjugated anti-mouse I-A$^b$ antibody, then analyzed by fluorescence-activated cell sorter Calibur using CELLQuest software (see FIG. 9C). The result indicated that the expression of I-A$^b$ molecule in peritoneal macrophages, in other words, blockage level of IFN-γ-induced cell proliferation was comparative among wild-type, MyD88- and TLR4-deficient mice.

5-6 (Analysis of Phagocytosis)

Macrophages of wild-type, MyD88- and TLR4-deficient mice added with 0.025% of fluorescent latex beads (0.75 μm) (Polyscience) were cultured for 2 hours at 37° C. in a $CO_2$ incubater. Then the culture materials were washed vigorously three times with PBS to remove non-phagocytosed beads and incubated with PBS containing 2.5% of formaldehyde for 20 minutes, and fixed with formaldehyde. Visualization of these fixed cells with Axiophoto microscope (Carl Zeiss, Inc.) showed that peritoneal macrophages of both TLR4- and MyD88-deficient mice phagocytosed the latex particles, and therefore, that phagocytic ability of the macrophages of TLR4- and MyD88-deficient mice were not impaired by these other stimuli.

5-7 (Responsiveness to LPS of *Porphyromonas gingivalis*)

As LPS of *Porphyromonas gingivalis* shows some reaction in its ability to activate cells of LPS-hyporesponsive C3H/HeJ mice (J. Immunol. 158, 1997, 4430–6), responsiveness of each mouse to LPS of *Porphyromonas gingivalis* was examined as in the case with *Salmonella minnesota* Re-595. In macrophages of wild-type mice, TNF-α was induced in response to LPS of *Porphyromonas gingivalis* in a dose-dependent manner. However, macrophages of TLR4-deficient mice were hyporesponsive like those of C3H/HeJ mice, and only showed the TNF-α producibility which was about one third of that of wild-type mice macrophages. In contrast, macrophages of MyD88-deficient mice did not produce any detectable TNF-α, even when stimulated with high concentration of LPS (see FIG. 10A).

Figure 10:
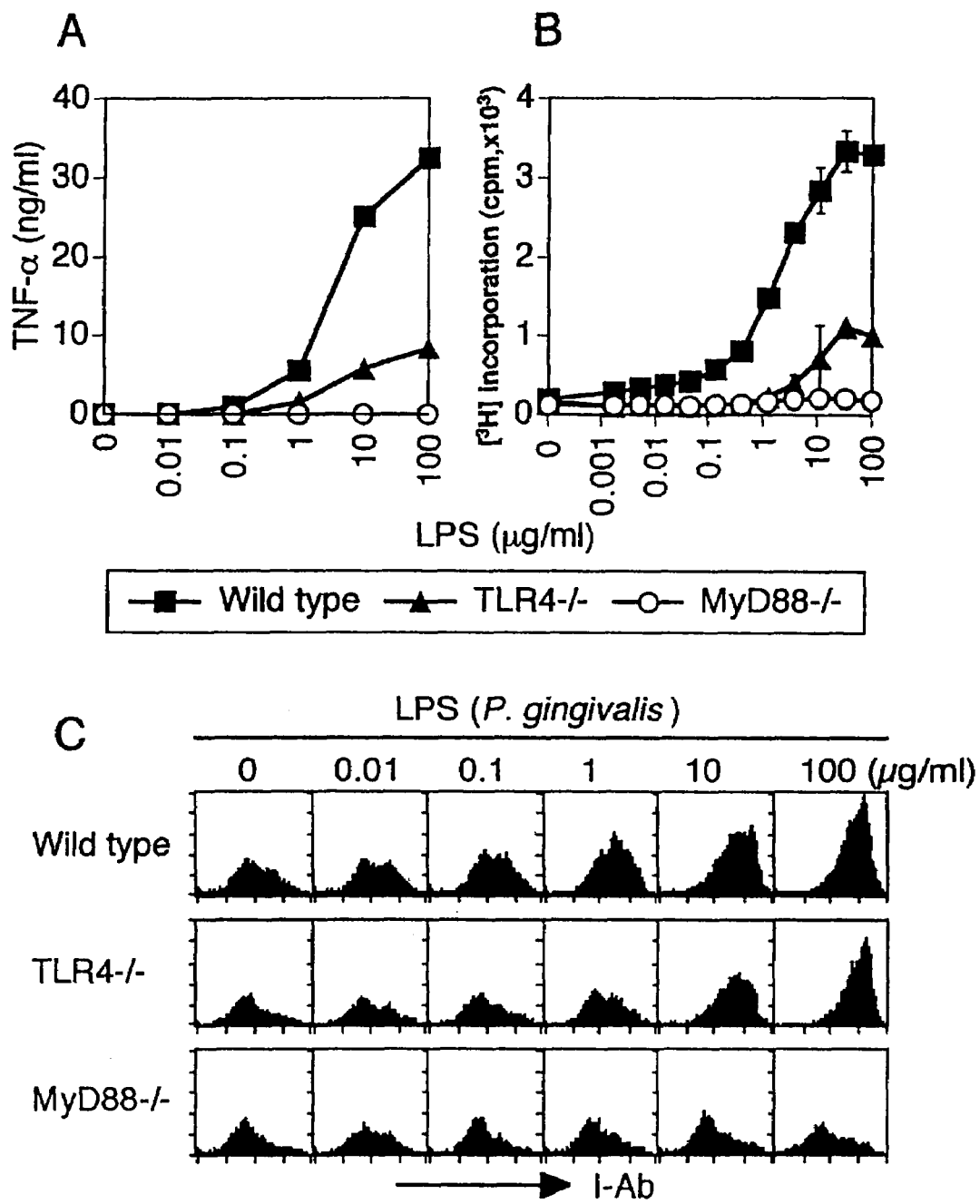
FIG. 10(A–C) is a graph showing the results of responsiveness of macrophages and splenic B cells of the MyD88 knockout mice, the wild-type mice and the TLR4 knockout mice of the present invention to *Porphyromonas gingivalis*.

Splenic B cells of TLR4-deficient mice exhibited low level proliferative response to LPS of *Porphyromonas gingivalis* 381, and enhanced the expression of I-A$^b$ molecule of splenic B cells, however, splenic B cells of MyD88-deficient mice did not exhibit proliferative response and the expression of I-A$^b$ molecule could not confirmed (see FIGS. 10B and C). Further, the same results were obtained with lipid A of *Porphyromonas gingivalis* 381. This indicates that TLR4-deficient mice are hyporesponsive and MyD88-deficient mice are unresponsive to LPS of *Porphyromonas gingivalis*. In addition, it has been found that MyD88 is essential for the signaling induced by LPS of *Porphyromonas gingivalis*, whereas TLR4 shows partial contribution.

5-8 (Responsiveness to LPS of *Escherichia coli* O55:B5)

Figure 11:
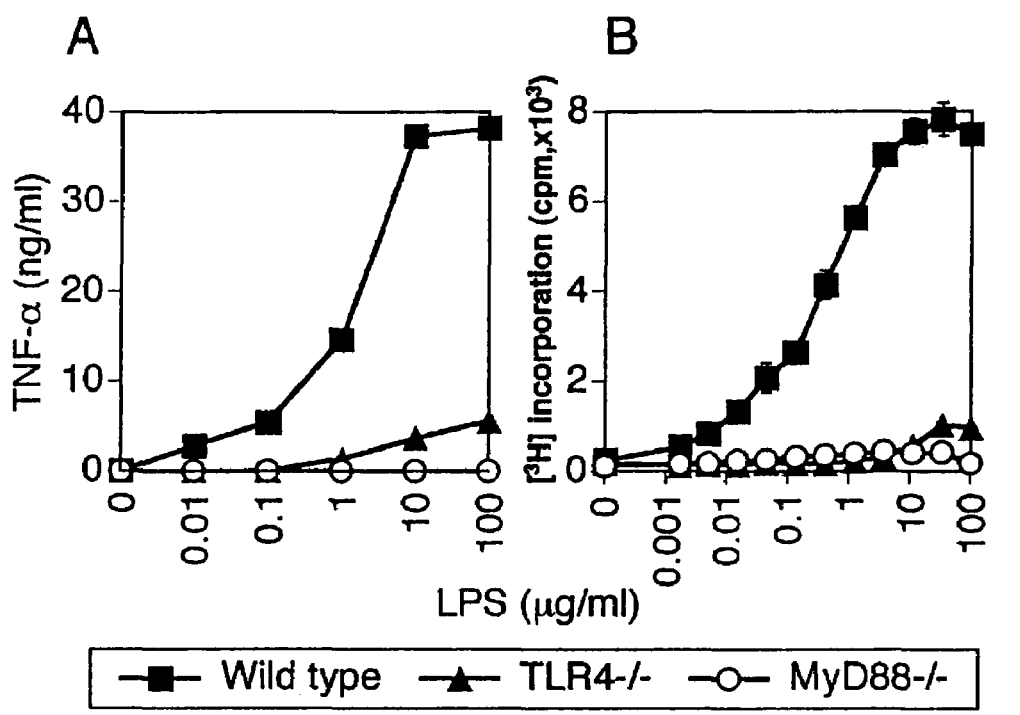
FIG. 11(A–C) is a graph showing the results of responsiveness of macrophages and splenic B cells of the MyD88 knockout mice, the wild-type mice and the TLR4 knockout mice of the present invention to *Escherichia coli* O55:B5.
Figure 11:
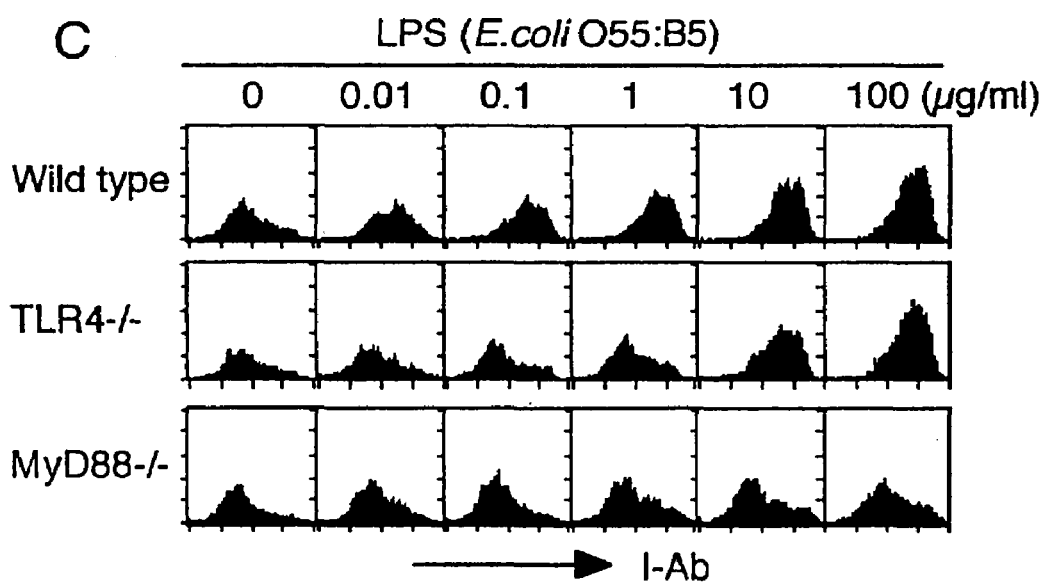

Responsiveness to LPS of *Escherichia coli* O55:B5 was examined as in the case with *Salmonella minnesota* Re-595. The responsiveness to LPS of *Escherichia coli* (O55:B5) was impaired in peritoneal macrophages of both TLR4- and MyD88-deficient mice, compared with those of wild-type mice (FIG. 11A). However, when stimulated with high concentration of LPS, macrophages of TLR4-deficient mice produced a small amount of TNF-α. In contrast, macrophages of MyD88-deficient mice did not produce TNF-α even when stimulated with high concentration of LPS.

Similar tendencies were observed in proliferative responses in splenic B cells of these mice (see FIG. 11B). Furthermore, when stimulated with LPS at a concentration over 10 μg/ml, splenic B cells of TLR4-deficient mice showed a certain expression level of I-A$^b$ molecule similar to the level shown by splenic B cells of wild-type mice. In contrast, splenic B cells of MyD88-deficient mice did not show I-A$^b$ molecule expression even when stimulated with LPS at a concentration of 100 μg/ml (see FIG. 1C). As in the case of stimuli with LPS of *Porphyromonas gingivalis*, these results indicate that TLR4-deficient mice are hyporesponsive and MyD88-deficient mice are unresponsive to LPS of *Escherichia coli* (O55:B5).

5-9 (Responsiveness to Peptidoglycan)

It has been reported that Peptidoglycan (PGN), which is a major cell wall component of Gram-positive bacteria, activates macrophages (J. Immunol. 155, 1995, 2620–30, Infect. Immun. 62, 1994, 2715–21). Therefore, responsiveness to PGN of *Staphylococcus aureus* (Fluka) was examined as in the case with *Salmonella minnesota* Re-595. When stimulated with PGN, peritoneal macrophages of TLR4-deficient mice produced TNF-α in a dose-dependent manner to almost the same extent as macrophages of wild-type mice. In contrast, macrophages of MyD88-deficient mice did not produce TNF-α even when stimulated with high concentration of PGN (see FIG. 12A).

Figure 12:
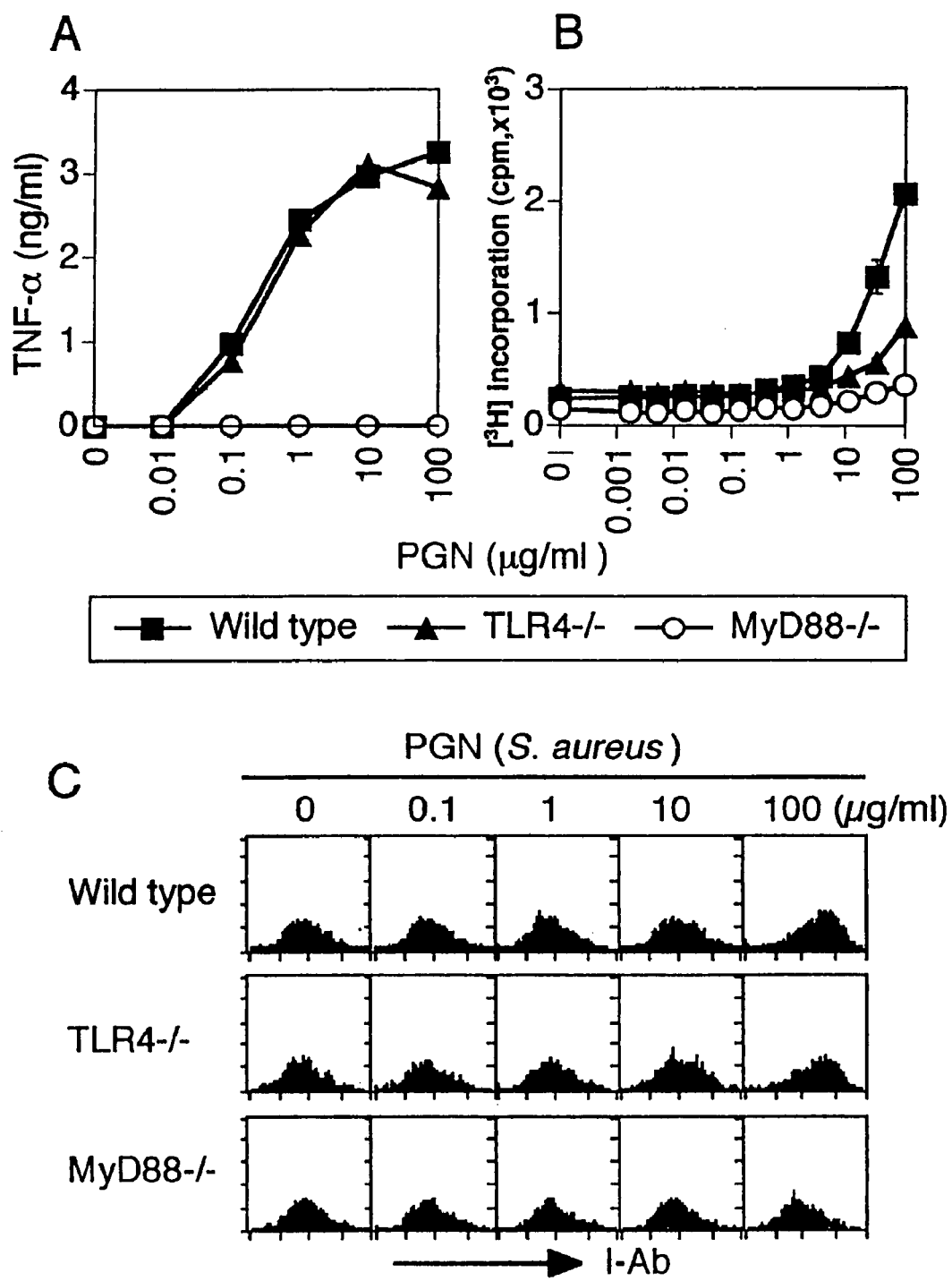
FIG. 12(A–C) is a graph showing the results of responsiveness of macrophages and splenic B cells of the MyD88 knockout mice, the wild-type mice and the TLR4 knockout mice of the present invention to peptidoglycan.

When stimulated with PGN of *Staphylococcus aureus*, splenic B cells of wild-type mice displayed proliferative responses, and the proliferative response was severely impaired in peritoneal macrophages of MyD88-deficient mice compared with those of wild-type mice, but in TLR4-deficient mice, the proliferative response was not severely impaired as in MyD88-deficient mice (see FIG. 12B). Further, when stimulated with PGN at a concentration over 10 μg/ml, splenic B cells of TLR4-deficient and wild-type mice showed enhancement of I-A$^b$ molecule expression. In contrast, splenic B cells of MyD88-deficient mice did not show enhancement of I-A$^b$ molecule expression even when stimulated with PGN at a concentration of 100 μg/ml (see FIG. 12C). Thus, TLR4-deficient mice showed almost the same response to PGN of *Staphylococcus aureus* as wild-type mice, while MyD88-deficient mice showed no responsiveness.

5-10 (Responsiveness to Lipoteichoic Acid)

As lipoteichoic acid (LTA) is a cell wall component of Gram-positive bacteria and induces activation of monocytes and macrophages (Infect. Immun. 62, 1994, 2715–21), responsiveness to LTA of *Streptococcus pneumoniae* was examined as in the case with *Salmonella minnesota* Re-595. Peritoneal macrophages of wild-type mice increased production of TNF-α in response to LTA in a dose-dependent manner. In contrast, macrophages of MyD88-deficient mice did not produce TNF-α even when stimulated with high concentration of LTA. In comparison with peritoneal macrophages of wild-type mice, TNF-α production was also impaired in those of TLR4-deficient mice, however, TNF-α was induced when stimulated with 100 µg/ml of LTA (see FIG. 13A).

Figure 13:
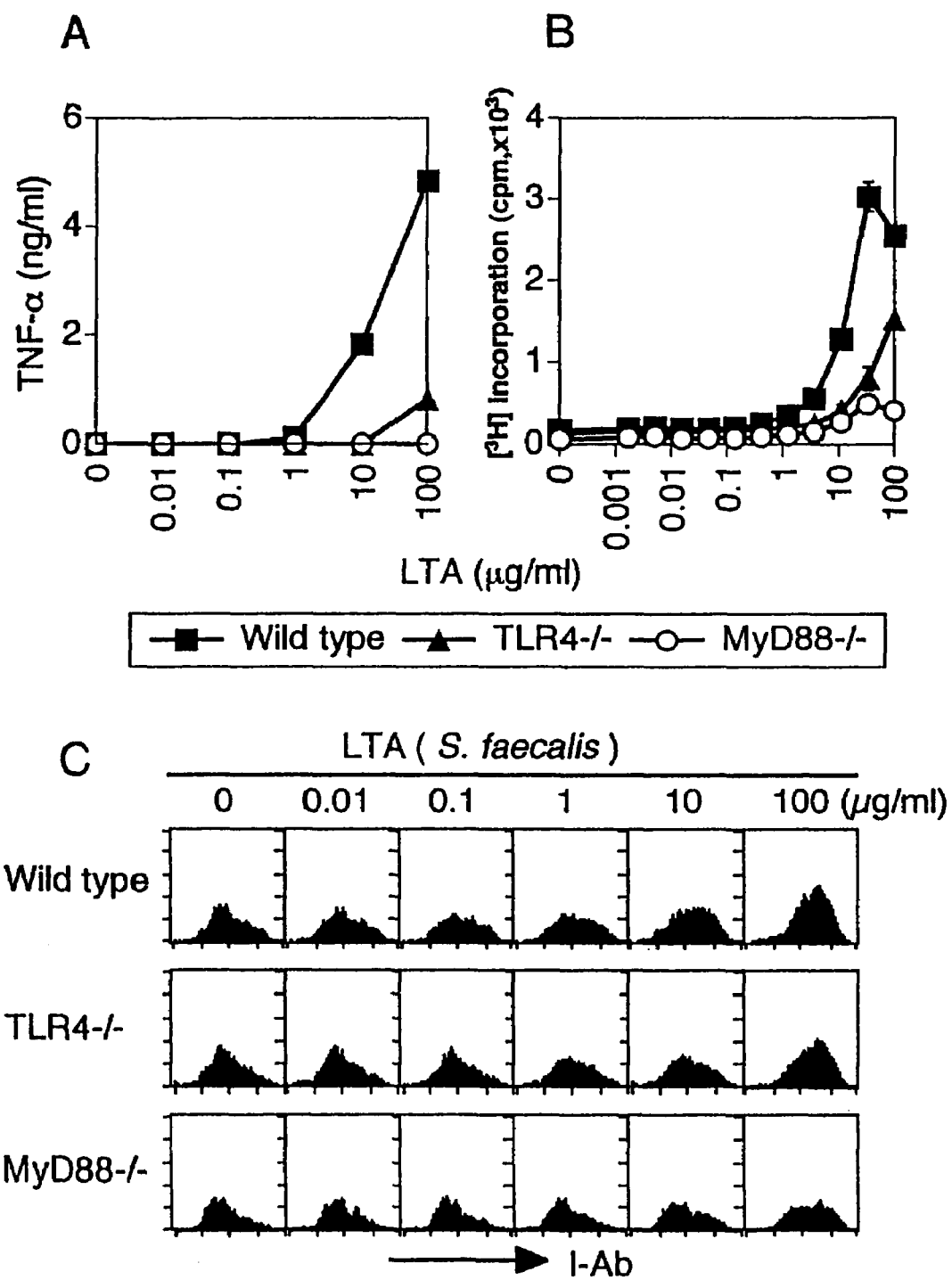
FIG. 13(A–C) is a graph showing the results of responsiveness of macrophages and splenic B cells of the MyD88 knockout mice, the wild-type mice and the TLR4 knockout mice of the present invention to lipoteichoic acid.

Next, proliferative responses and enhancement of I-A$^b$ molecule expression in splenic B cells of these mice in response to stimulation from LTA of *Streptococcus pneumoniae* was analyzed (see FIG. 13B). The results indicated that splenic B cells of wild-type mice enhanced their response to LTA in a dose-dependent manner, whereas splenic B cells of MyD88-deficient mice exhibited a severely defective proliferative response to LTA. Though splenic B cells of TLR4-deficient mice also exhibited an impaired proliferative response, they exhibited proliferative response when stimulated with high concentration of LTA. Further, in splenic B cells of wild-type and TLR4-deficient mice, enhancement of I-A$^b$ molecule expression was also observed on the cell surface, whereas no enhancement was observed in those of MyD88-deficient mice (see FIG. 13C). This indicates that MyD88-deficient mice are unresponsive to stimulation from LTA of *Streptococcus pneumoniae*.

5-11 (Responsiveness to Whole Cell Lysates of *Mycobacterial tuberculosis*)

As cell wall components of *Mycobacterial tuberculosis*, especially lipoarabinomannan, are known to induce activation of myeloidcells (J. Immunol. 149, 1992, 541–7, J. Clin. Invest. 91, 1993, 2076–83), responsiveness to whole cell lysates of Mycobacterial tuberculosis was examined as in the case with *Salmonella minnesota* Re-595. Macrophages of wild-type mice produced TNF-α in response to the whole lysates in a dose-dependent manner. Macrophages of TLR4-deficient mice also exhibited TNF-α production though the production amount was smaller than those of wild-type mice. However, macrophages of MyD88-deficient mice did not produce TNF-α in response to the whole cell lysates of Mycobacterial tuberculosis at a high concentration (see FIG. 14A).

Figure 14:
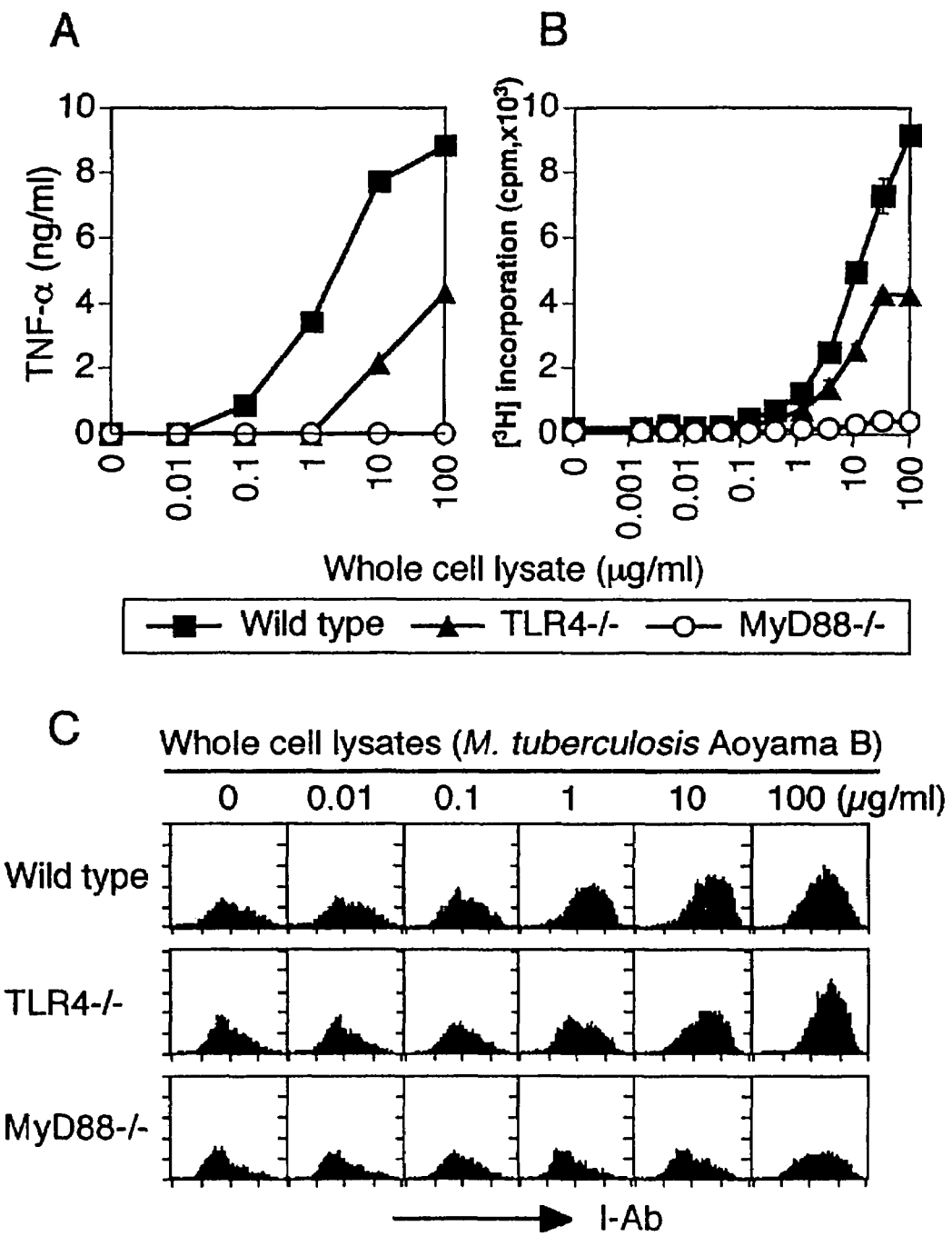
FIG. 14(A–C) is a graph showing the results of responsiveness of macrophages and splenic B cells of the MyD88 knockout mice, the wild-type mice and the TLR4 knockout mice of the present invention to whole cell lysates of *Mycobacterium tuberculosis*.

Next, responsiveness of these mice to stimulation from whole cell lysates of Mycobacterial tuberculosis was examined. Splenic B cells of wild-type mice exhibited enhancement of proliferative responses and I-A$^b$ molecule expression on the surface of the cells in response to the whole cell lysates in a dose-dependent manner. Splenic B cells of TLR4-deficient mice also showed proliferative responses and I-A$^b$ molecule expression, although these responses were lower than those of splenic B cells of wild-type mice. In contrast, splenic B cells of MyD88-deficient mice displayed severely impaired proliferative responses and enhancement of I-A$^b$ molecule expression, indicating that they are unresponsive to the whole cell lysates (FIGS. 14B and C).

5-12 (Responsiveness to Other Bacterial Cell Wall Components)

Responsiveness of wild-type, TLR4- and MyD88-deficient mice to other bacterial cell wall components [LPSs of *Klebsiella pneumoniae*, *Pseudomonas aeruginosa* 10, *Salmonella typhimurium*, *Shigella flexneri*, *Vibrio cholerae* and the like, and PGN of *Staphylococcus epidermidis*, which is provided from Shigeo Kawata of Dainippon Pharmaceutical Co.] was examined in a same manner as aforementioned. The results are shown in Table 1. This Table 1 shows that MyD88-deficient mice are unresponsive to all bacterial cell components.

TABLE 1

| Sample | Responsiveness of mice | | |
|---|---|---|---|
| LPS | wild-type | TLR4−/− | MyD88−/− |
| *Escherichia coli* O55:B5 | ++ | + | − |
| *Klebsiella pneumoniae* | ++ | − | − |
| *Porphyromonas gingivalis* | ++ | + | − |
| *Pseudomonas aeruginosa* | ++ | + | − |
| *Salmonella minnesota* Re595 | ++ | − | − |
| *Salmonella typhimurium* | ++ | + | − |
| *Serratia marcescens* | ++ | + | − |
| *Shigella flexneri* | ++ | + | − |
| *Vibrio cholerae* | ++ | + | − |
| PGN | | | |
| *Staphylococcus aureus* | ++ | ++ | − |
| *Staphylococcus epidermidis* | ++ | + | − |
| LTA | | | |
| *Streptococcus faecalis* | ++ | + | − |
| whole cell lysates of | | | |
| *Mycobacterium tuberculosis* | | | |
| *Mycobacterium tuberculosis* | ++ | + | − |

It has been found that LPS can be classified into two types: one type includes LPSs which utilize TLR4 as their unique signaling receptor and show unresponsiveness (LPSs of *Salmonella minnesota* Re595, *Klebsiella pneumoniae* and the like); another type includes LPSs which show hyporesponsiveness to TLR4-deficient mice (LPSs of *Porphyromonas gingivalis*, *Escherichia coli* O55:B5, *Pseudomonas aeruginosa*, *Shigella flexneri*, *Salmonella typhimurium*, *Vibrio cholerae* and the like). Since MyD88-deficient mice show no responsiveness to these latter LPSs, it is presumed that the recognition and signaling of these LPSs are mediated by both TLR4 and other TLRs, and/or by TLR-related receptors that use MyD88 as an adaptor molecule.

EXAMPLE 6

Generation of TLR2 Knockout Mice

TLR2 gene was screened from 129/SvJ mouse genomic library (Stratagene) using a probe derived from a mouse EST clone (accession number D77677) similar to human TLR2 gene, and subcloned into pBluescript vector (Stratagene), then characterized by restriction enzyme mapping and DNA sequencing. A targeting vector was constructed by replacing a gene fragment at an exon region 1.3 kb containing cytoplasmic domain of TLR2 gene with pMC1-neo (Stratagene) having Poly A signal. The targeting vector was flanked by a 4.8 kb 5' genomic fragment and a 1.0 kb 3' fragment and contained an HSV-tk cassette at the 5' terminal. The targeting vector was linearized with SalI and electroporated into E14.1 embryonic stem cells (ES cells). 120 clones resistant to G418 and gancyclovir were screened for homologous recombination by PCR and 9 clones were confirmed by Southern blot analysis using the probe indicated in FIG. 15A.

Figure 15:
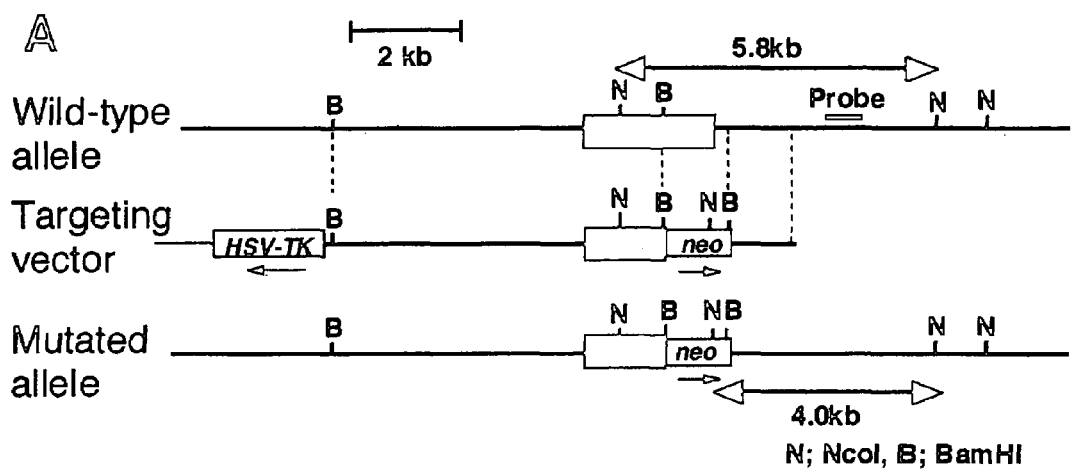
FIG. 15(A–C) is a graph showing gene maps of the TLR2 knockout mice and the wild-type mice of the present invention.
Figure 15:
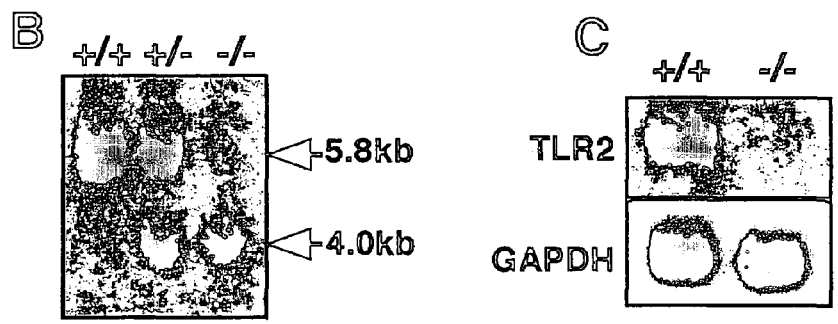

Chimeric mice were generated by microinjection of 3 targeted ES clones containing a homologously recombined mutant TLR2 allele into blastocysts of C57BL/6 mice. Male chimeric mice were bred to C57BL/6 females to produce heterozygous mice. The heterozygous mice were intercrossed to obtain homozygotes (FIG. 15B). TLR2-deficient mice of the present invention could be generated at the expected Mendelian ratio, and did not show any obvious abnormality until 20 weeks.

To confirm that the homologous recombination caused inactivation of the TLR2 gene, total RNA (15 μg) was extracted from peritoneal macrophages ($5 \times 10^6$) of wild-type (+/+) and TLR2 knockout (−/−) mice and then electrophoresed, transferred to a nylon membrane, and Northern blot analysis was conducted using cDNA specific to [$^{32}$P]-labelled TLR2, or cDNA specific to GAPDH (glycelaldehyde-3-phosphate dehydrogenase) as the method previously described (Immunity 9, 143–150, 1998). As a result, TLR2 mRNA was not detected in peritoneal macrophages of TLR2-deficient mice (FIG. 15C). In addition, it was shown that the expressions of CD3, B220, CD4, and CD8 in thymocytes and splenocytes of TLR2 knockout mice were not different from those of wild-type mice (data not shown).

EXAMPLE 7

Figure 16:
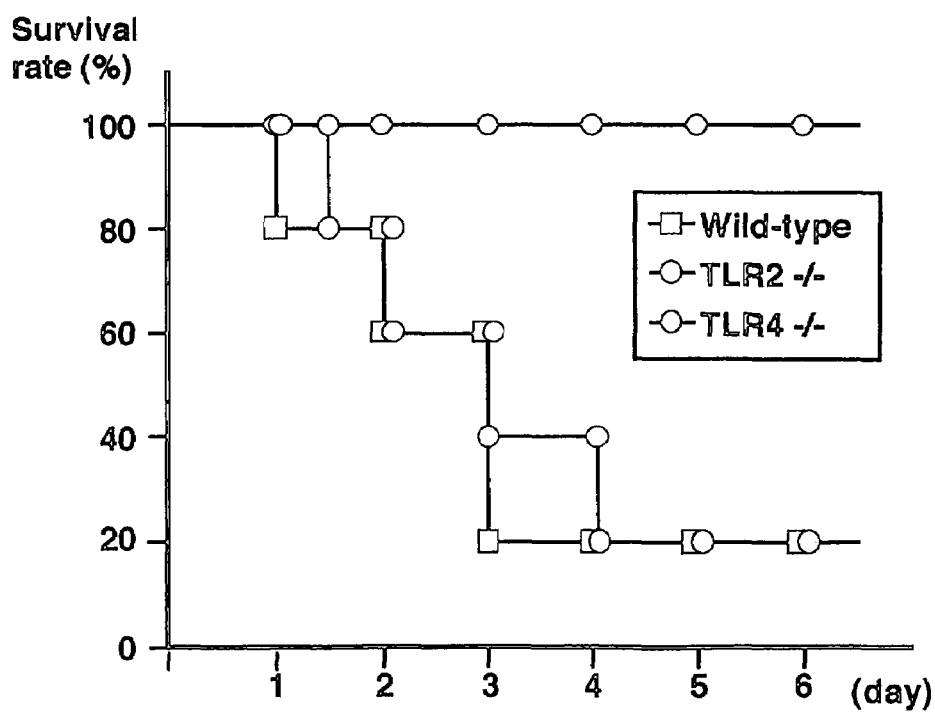
FIG. 16 is a graph showing survival indices of the TLR2 knockout mice and the wild-type mice of the present invention having an injection of LPS derived from *Escherichia coli*.

Responsiveness of TLR2 Knockout Mice to Endotoxin 1 mg of LPS derived from *Escherichia coli* (O55:B5) was injected into each of TLR2 knockout mice (n=5), TLR4 knockout mice (n=5) and wild-type mice (n=5) of the present invention, and LPS unresponsiveness was examined by their survival rate. The results are shown in FIG. 16. FIG. 16 confirms that though TLR2 knockout mice (TLR2−/−) and wild-type mice of the present invention responded to LPS and almost all of them died within 4 days after injection, none of TLR4 knockout mice (TLR4−/−) died even after 6 days after injection, and that TLR4 knockout mice are unresponsive to endotoxin.

EXAMPLE 8

Responsiveness of TLR2 Knockout Mice to Cell Components of Gram-Negative Bacteria Each of TLR2 knockout (TLR2−/−), TLR4 knockout (TLR4−/−) and wild-type (wild-type) mice were intraperitoneally injected with 2 ml of 4% thioglycollate medium (DIFCO). Three days later, peritoneal exudate cells were isolated from the peritoneal cavity of each mouse. These cells were cultured in RPMI1640 medium (GIBCO) supplemented with 10% fetal bovine serum (GIBCO) for 2 hours at 37° C. and washed with ice-cold Hank's buffered salt solution (HBSS; GIBCO) to remove nonadherent cells. Adherent cells were used as peritoneal macrophages for following experiments.

Each of obtained peritoneal macrophages were cultured for 24 hours with 1.0 ng/ml of synthetic lipid A derived from *Escherichia coli* (compound 506; Daiichi Pure Chemicals) or LPS derived from *Salmonella minnesota* Re-595 (Sigma) in the presence or absence of IFN-γ (30 unit/ml). Synthetic lipid A, which was soluble in endotoxin-free water and containing 0.025% of triethylamine, was used as said synthetic lipid A. After the culture, production amounts of IL-6 (FIG. 17A), TNF-α (FIG. 17B) and $NO_2^-$ (FIG. 17C) in culture supernatants were measured. Production amount of IL-6 was measured by enzyme-linked immunosorbent assay (ELISA; ENDOGEN), and that of TNF-α was measured by ELSIA, according to manufacturer (Genzyme)'s instructions, and that of $NO_2^{31}$ was measured by the Greiss method using $NO_2/NO_3$ Assay Kit (Dojindo Laboratories).

These results indicate that macrophages of wild-type mice and TLR2 knockout mice showed similar responsiveness to LPS and lipid A, and produced IL-6 and TNF-α, and it was confirmed that production of TNF-α would be further increased when IFN-γ was added to LPS or lipid A before the culture. By contrast, macrophages of TLR4 knockout mice produced neither IL-6 nor TNF-α. Further, production of $NO_2^-$ was confirmed by culturing macrophages of wild-type and TLR2 knockout mice with IFN-γ-added lipid A or LPS. The obtained results were same as those aforementioned even in the case the injection amount of lipid A or LPS was arranged to be 1 μg/ml (data not shown).

Figure 17:
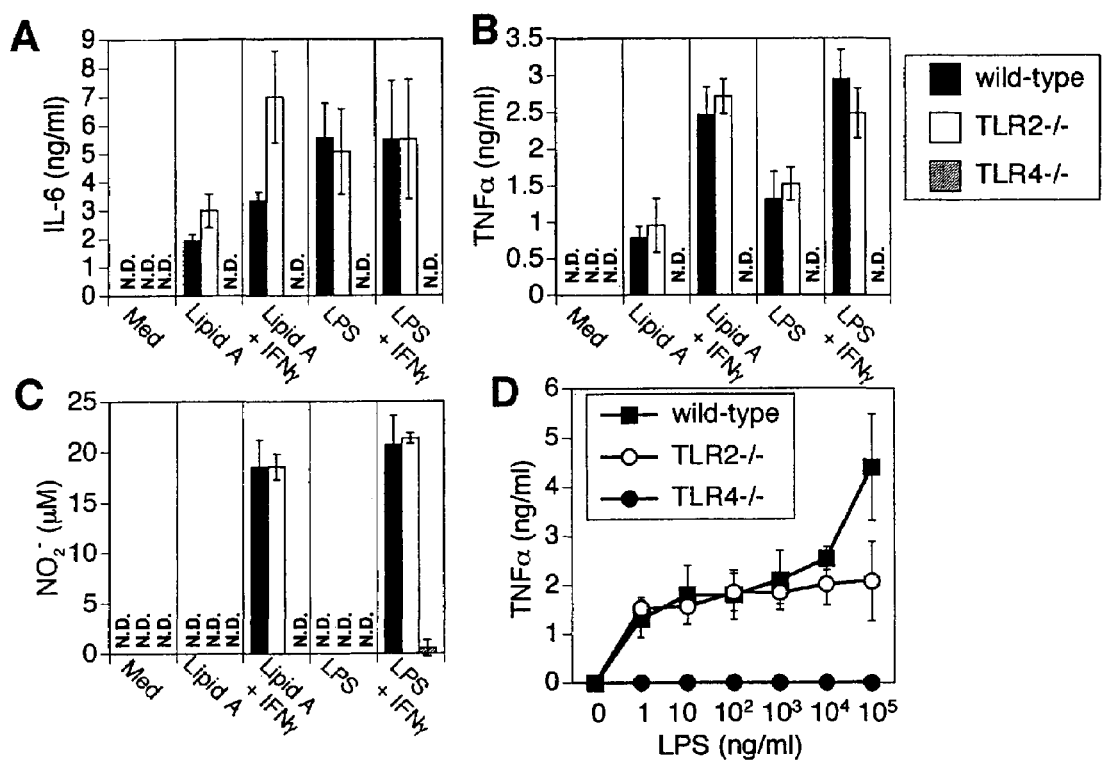
FIG. 17(A–D) is a graph showing lipid A- or LPS-induced production amount of IL-6, TNF-α or $NO_2^-$ in the TLR2 knockout mice, the wild-type mice and the TLR4 knockout mice of the present invention.

Next, each of peritoneal macrophages of wild-type, TLR2 knockout and TLR4 knockout mice were cultured in the presence of LPS derived from *Salmonella minnesota* Re-595 at various concentrations shown in FIG. 17D, and production of TNF-α was measured. The results indicate that macrophages of wild-type mice and TLR2 knockout mice showed similar tendency to increase in response to LPS in a dose-dependent manner, while macrophages of TLR4 knockout mice produced no TNF-α in response to any concentration of LPS.

EXAMPLE 9

Responsiveness to LPS of *Salmonella minnesota* Re-595

Figure 18:
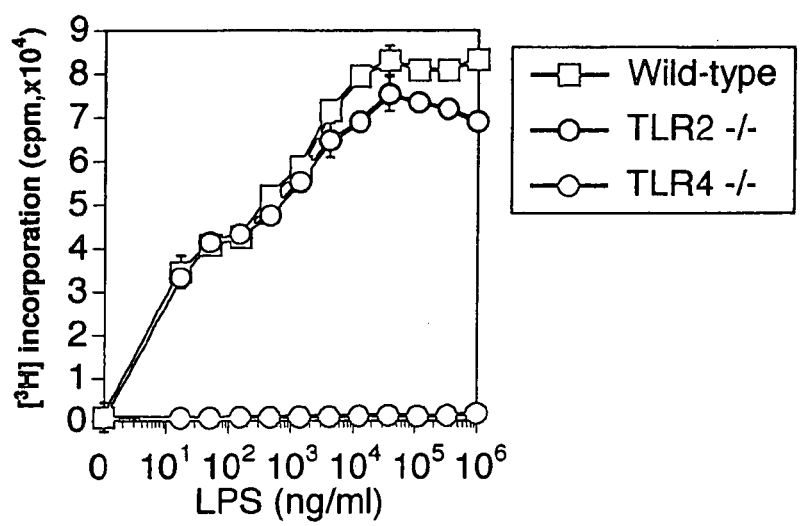
FIG. 18(A–B) is a graph showing the results of responsiveness of splenic B cells of the TLR2 knockout mice, the wild-type mice and the TLR4 knockout mice of the present invention to LPS derived from *Salmonella minnesota* Re-595.
Figure 18:
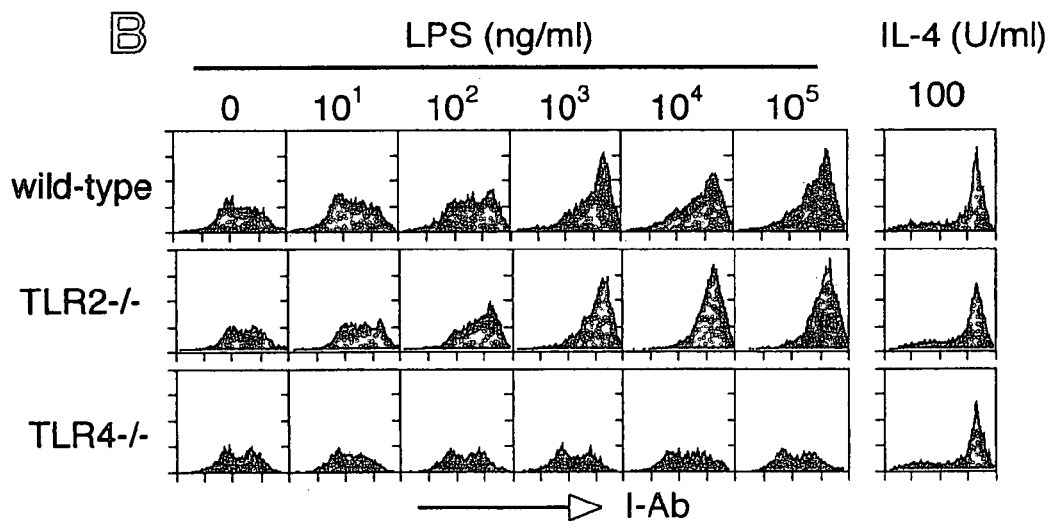

Responsiveness of splenocytes of various mice (wild-type, TLR2−/− and TLR4−/−) to LPS of *Salmonella minnesota* Re-595 were examined. Splenocytes ($1 \times 10^5$) of each mouse were isolated and then cultured and stimulated in 96-well plates with various concentrations of LPS shown in FIG. 18A. 1 μCi of [$^3$H]-thymidine (DuPont) was added 40 hours after the onset of the culture, and cells were further cultured for 8 hours, then [$^3$H] uptake was measured by a β scintillation counter (Packard) (FIG. 18A). As a result, the cell proliferative response was promoted in response to LPS in a dose-dependent manner in splenocytes of wild-type and TLR2 knockout mice as well. By contrast, whatever the concentration of LPS as a stimulus would be, no LPS-induced cell proliferative response was observed in splenocytes of TLR4-deficient mice.

In addition, the expression of major histocompatibility complex (MHC) class II (I-A$^b$) on the surface of B cells in response to Re-595 LPS was examined by flow cytometry. Splenic B cells ($1 \times 10^5$) of each of wild-type, TLR2 knockout (2−/−) and TLR4 knockout (4−/−) mice were isolated and cultured for 48 hours in 96-well plates with various concentrations (0, $10^1$, $10^2$, $10^3$, $10^4$ or $10^5$ ng/ml) of LPS or 100 U/ml of IL-4. After the culture, the cells were collected and stained by combining I-A$^b$ molecule on the surface of the cells and FITC-labelled antibody which is constructed by combining phycoerythrin (PE; PharMingen)-conjugated anti-B220 antibody or biotinylated anti-mouse I-A$^b$ antibody (PharMingen) and fluorescein isocyanate (FITC; PharMingen)-conjugated streptavidin. The stained cells were analyzed on fluorescence-activated cell sorter Calibur (FACS Calibur) using CELLQuest software (Becton Dickinson) (FIG. 18B). As a result, Re-595 LPS enhanced the expression of I-A$^b$ molecule on the surface of splenic B cells of wild-type and TLR2 knockout mice. In contrast, I-A$^b$ molecule expression in splenic B cells of TLR4-deficient mice were not enhanced by Re-595 LPS, even when stimulated with high concentration of LPS ($10^5$ ng/ml). The above-mentioned results indicate that TLR2 knockout mice show responsiveness to LPS as wild-type mice did. When stimulated with IL-4, each knockout mice show normal expression of I-A$^b$ molecule on the surface of splenic B cells.

EXAMPLE 10

Unresponsiveness of Macrophages of TLR2 Knockout Mice to Cell Wall Components Derived from Gram-Positive Bacteria Responsiveness of each peritoneal macrophages of said wild-type (wild-type), TLR2 knockout (TLR2−/−), TLR4 knockout (TLR4−/−) mice and the like to cell wall components derived from Gram-positive bacteria were examined with prepared cell wall specimens of *S. aureus, C. diphtheriae* and *N. coeliaca*. The cell specimens were prepared in accordance with the method previously described (Biken J. 18, 77–92, 1975, Infect. Immun. 38, 817–824, 1982), that is, bacterial cells grown under appropriate cultural conditions were disrupted with either a Braun mechanical cell homogenizer (model MSK; B. Braun Apparatebau) or a Dyno-Mill (type KDL; Willy A, Biochofen Manufactureing Engineers). A crude cell wall fraction obtained by differential centrifugation of a disrupted cell suspension was purified and prepared by removal of components noninherent in cell walls with protease treatment.

Figure 19:
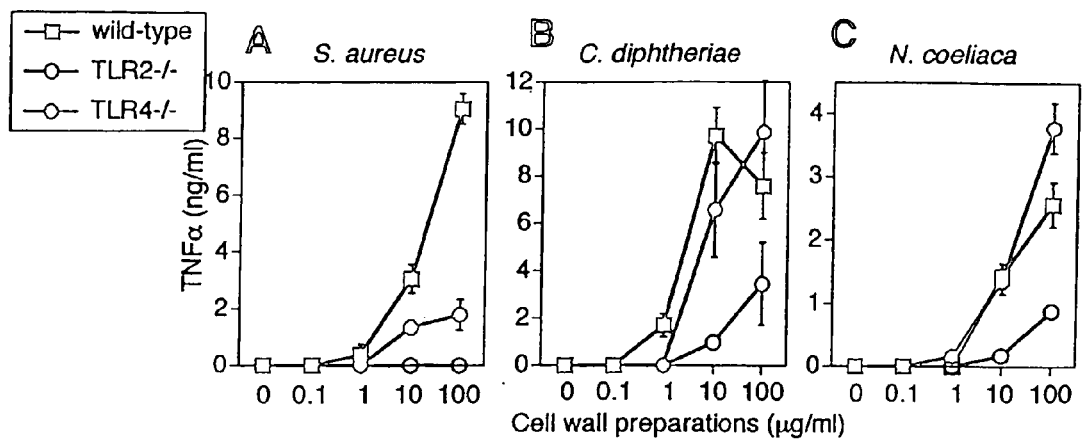
FIG. 19(A–C) is a graph showing the results of responsiveness of peritoneal macrophages of the TLR2 knockout mice, the wild-type mice and the TLR4 knockout mice of the present invention to cell wall fractions of Gram-positive bacteria.

Peritoneal macrophages of each mouse were cultured for 24 hours in the presence of various concentrations (0, 0.1, 1, 10 or 100 µg/ml) of said preparations and stimulated, then concentration of tumor necrosis factor (TNF-α) released from each macrophage was measured by ELISA (FIG. 19). By these results, it has been found that production of TNF-α in response to cell wall components derived from Gram-positive bacteria was more impaired in macrophages of TLR2 knockout mice than in those of wild-type and TLR4 knockout mice.

EXAMPLE 11

Figure 20:
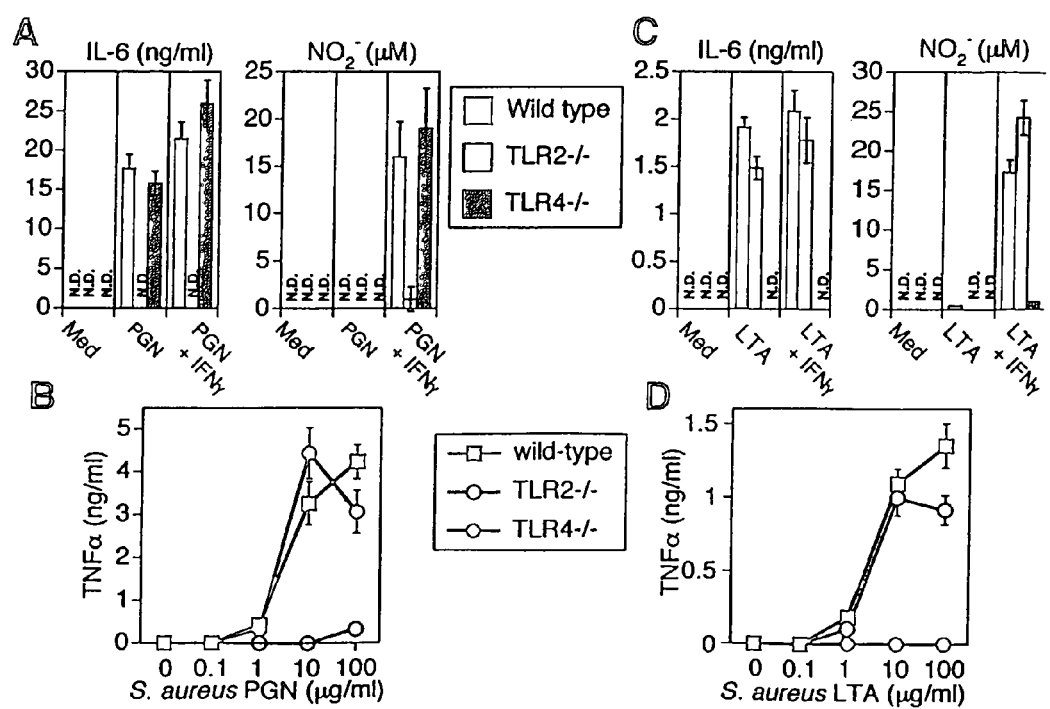
FIG. 20(A–D) is a graph showing PGN- or LTA-induced production amount of IL-6, $NO_2^-$ or TNF-α in the TLR2 knockout mice, the wild-type mice and the TLR4 knockout mice of the present invention.

Responsiveness of TLR2 Knockout Mice to Cell Wall Components of Gram-Positive Bacteria Next, it was investigated that which cell wall component of Gram-positive bacteria activated macrophages via TLR2. As it has been reported that both peptidoglycan, which is a cell wall component of Gram-positive bacteria, and lipoteichoic acid (LTA) activate monocytes/macrophages (Infect. Immun. 60, 3664–3672, 1992, Immunity 1, 509–516, 1994, J. Biol. Chem. 271, 23310–23316, 1996, Infect. Immun. 64, 1906–1912, 1996), production amounts of IL-6 and $NO_2^-$ in response to peritoneal macrophages of various kinds of mouse were measured in accordance with the same method as in example 8, with 10 µg/ml of *Staphylococcus aureus* PGN (Fluka; FIG. 20A) or 10 µg/ml of *Staphylococcus aureus* LTA (Sigma; FIG. 20C). Further, production of TNF-α in peritoneal macrophages of various kinds of mouse in response to PGN (FIG. 20B) or LTA (FIG. 20D) were measured in accordance with the same method as in example 10.

The results shown in FIG. 20A indicates that: peritoneal macrophages of wild-type and TLR4 knockout mice produced IL-6 in response to PGN, in contrast, those of TLR2 knockout mice produced no IL-6; $NO_2^-$ was produced when peritoneal macrophages of wild-type and TLR4 knockout mice were cultured with PGN in the presence of IFN-γ, in contrast, no $NO_2^-$ was produced when those of TLR2 knockout mice were used; IL-6 was produced in peritoneal macrophages of wild-type and TLR2 knockout mice in response to LTA, in contrast, no IL-6 was produced in those of TLR4 knockout mice (FIG. 20C); $NO_2^-$ was produced when peritoneal macrophages of wild-type and TLR2 knockout mice were cultured with LTA in the presence of IFNγ, in contrast, no $NO_2^-$ was produced when those of TLR4 knockout mice were used (FIG. 20C).

As shown in FIG. 20B, peritoneal macrophages of TLR4 knockout mice, as well as those of wild-type mice, increased production of TNF-α in response to PGN in a dose-dependent manner, in contrast, those of TLR2 knockout mice showed substantial impairment in production of TNF-α, indicating that TLR2 knockout mice were unresponsive to PGN. As shown in FIG. 20D, peritoneal macrophages of TLR2 knockout mice, as well as those of wild-type mice, induced production of TNF-α in response to LTA in a dose-dependent manner, in contrast, no TNF-α was produced in those of TLR4 knockout mice, indicating that TLR4 knockout mice were unresponsive to LTA. These results demonstrate that PGN, which is a cell wall component of Gram-positive bacteria, activates macrophages via TLR2, and that LTA activates macrophages via TLR4.

EXAMPLE 12

LPS or PGN-Stimulated In Vitro Kinase Assay and Western Blot Analysis

Figure 21:
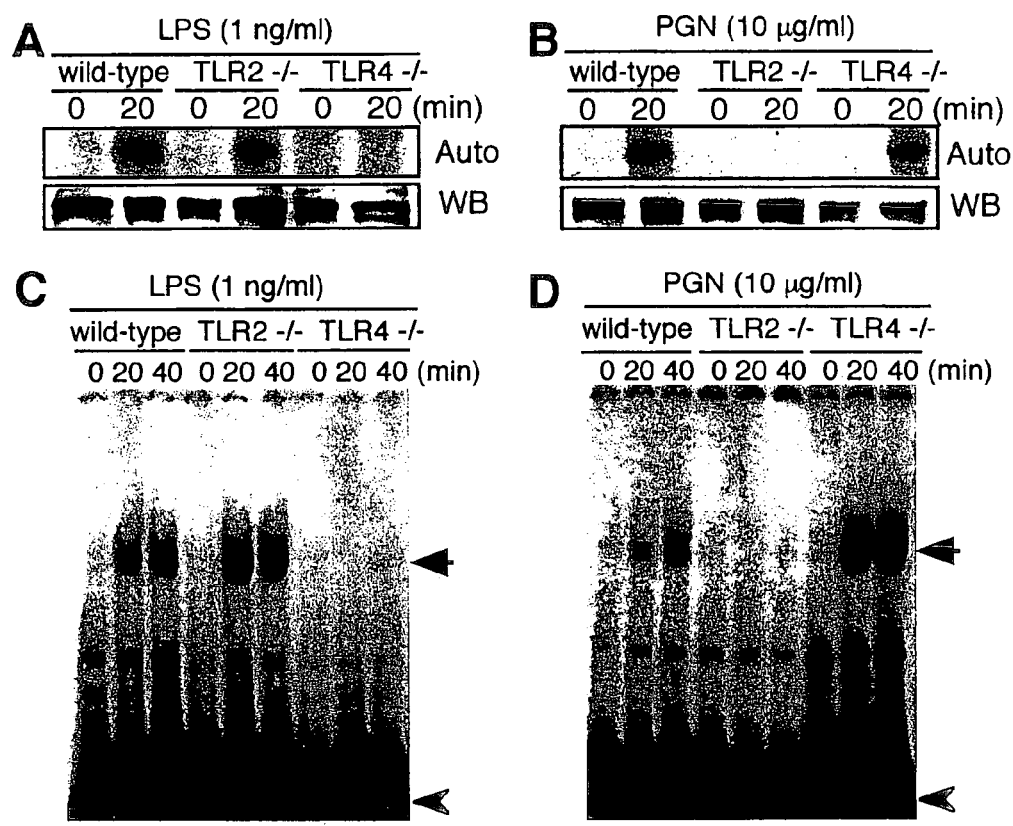
FIG. 21(A–D) is a graph showing the results of LPS- or PGN-stimulated in vitro kinase assay, Western blot analysis and electrophoretic mobility shift assay in the TLR2 knockout mice, the wild-type mice and the TLR4 knockout mice of the present invention.

TLR family members are known as intracellular signaling molecules which activate a serine-threonine kisase IRAK via an adapter protein MyD88, and subsequently activate rel-type transcription factor, NF-$_κ$B (Mol. Cell 2, 253–258, 1998, J. Exp. Med. 187, 2097–2101, 1998, Immunity 11, 115–122, 1999). Whether LPS and PGN activate the intracellular signaling molecules was examined as follows: peritoneal macrophages (1×10$^6$) of various kinds of mouse were stimulated with 1 ng/ml of LPS of *Salmonella minnesota* Re-595 or 1 µg/ml of PGN of *Staphylococcus aureus* for the period indicated in FIG. 21; these bacterial cell components were lysed in lysis buffer (buffer containing Triton X-100 at a final concentration of 1.0%, 137 mM of NaCl, 20 mM of Tris-HCl, 5 mM of EDTA, 10% of glycerol, 1 mM of PMSF, 20 µg/ml of Aprotinin, 20 µg/ml of Leupeptin, 1 mM of $Na_3VO_4$, and 10 mM of β-glycerophosphate; pH 8.0); the cells were immunoprecipitated with anti-IRAK antibody (Hayashibara Biochemical Laboratories, Inc.); in vitro kinase assay were conducted as previously described (Biochem. Biophys. Res. Commun. 234, 183–196, 1998, Immunity 11, 115–122, 1999); autophosphorylation of IRAK were measured (Auto shown in FIGS. 21A and B).

The lysates were dissolved by SDS-polyacrylamide gel electrophoresis and transferred to a nitrocellulose membrane. The membrane was blotted with anti-IRAK antibody (Transduction Laboratories) and visualized by using the enhanced chemiluminescence system (DuPont) (WB in FIGS. 21A and B). These results show that IRAK activation in response to LPS was observed in wild-type (wild-type) and TLR2 knockout (TLR2−/−) mice, but not observed in TLR4 knockout (TLR4−/−) mice. In contrast, IRAK activation in response to PGN was observed only in wild-type and TLR4 knockout mice. Thus indicates that LPS is recognized via TLR4, and that PGN is recognized via TLR2 respectively.

NF-$_κ$B activation in response to LPS or PGN was also investigated. Macrophages of various kinds of mouse were stimulated with said LPS or PGN, then nuclear extracts from the macrophages were purified and incubated with a probe specific to DNA binding site of NF-$_\kappa$B, and visualized by electrophoretic mobility shift assay as described previously (Immunity 9, 143–150, 1998). The results are shown in FIGS. 21C and D. Arrows in FIGS. 21C and D indicate the position of a complex comprised of NF-$_\kappa$B and the specific probe, and arrowheads indicate the position of specific probe only. As a result, DNA binding activity of NF-$_\kappa$B in response to LPS was detected in nuclear extracts from macrophages of wild-type and TLR2 knockout mice, but not in those of TLR4 knockout mice. In contrast, NF-$_\kappa$B activation in response to PGN was observed in macrophages of wild-type and TLR4 knockout mice but not in those of TLR2 knockout mice. Thus indicates that TLR4 is essential for LPS-induced NF-$_\kappa$B activation, and that TLR2 is essential for PGN-induced NF-$_\kappa$B activation.

EXAMPLE 13

Stereospecific Lipopeptide Synthesis and HPLC Purification of R- and S-MALP-2

The stereoisomers of S-(2,3-dihydroxypropyl)-L-cystein were synthesized as described previously (Int. J. Peptide Protein. Res. 38, 545, 1991) using two reagents, (S)-(−)-glycidol and (R)-(+)-glycidol (Sigma-Aldrich), which contain enantiomers purified to 99% or over respectively, as starting materials. The isomers of N$_\alpha$-fluorenylmethoxycarbonyl-protected S-[2(S), 3-bis(palmitoyloxy)propyl]-L-cystein and S-[2(R), 3-bis(palmitoyloxy) propyl]-L-cystein were synthesized respectively from these steroisomers and coupled according to the previously described method, and a carrier-bound fluorenylmethoxycarbonyl-protected peptide was obtained. 10 mg of crude MALP-2 was further purified in batch treatment by reversed phase HPLC using SP 250/10 Nucleosil 300-7 C8 column (Macherey & Nagel) and was eluted at 40° C. with a linear gradient of water/2-propanol containing 0.1% trifluoroacetic acid. Elution of active material was monitored by the NO release assay. The final product was characterized by mass spectroscopy and amino acid analysis for determination of the exact peptide content. MALP-2 was prepared to be a concentration of 1 mg/ml using a solution of water/2-propanol 1:1 (v/v) and stored at 4° C.

EXAMPLE 14

Figure 22:
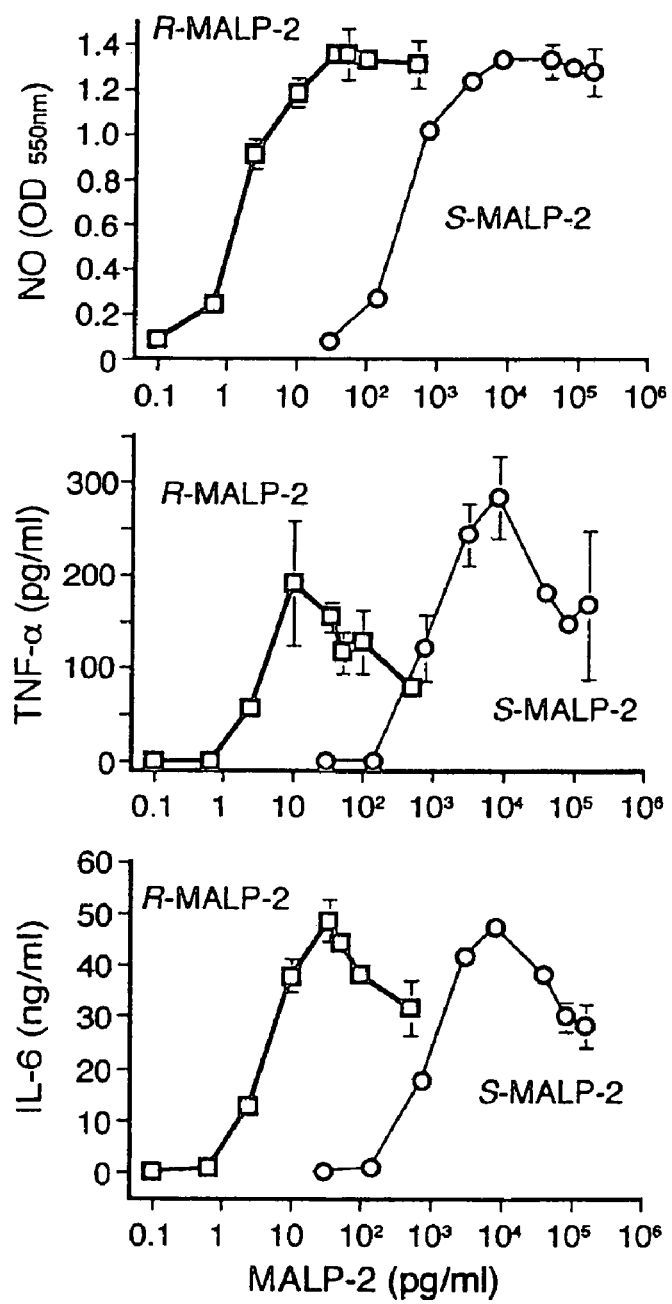
FIG. 22 is a graph showing the results of responsiveness of peritoneal macrophages of CH3/HeJ mice to lipopeptide MALP-2.

Responsiveness of Peritoneal Macrophages of CH3/Hej Mice to Lipoprotein/Lipopeptide PEC (peritoneal exudate cells) were isolated from endotoxin-hyporesponsive mice derived from CH3/HeJ, and these PEC ($6\times10^5$) were cultured overnight at 37° C. in 24-well cell culture plates having 1.25 ml of Dulbecco MEM medium (DMEM) which contained 5% of FCS and 25 μM of 2-mercaptoethanol. Peritoneal macrophages were prepared by removing nonadherent cells from the cultured material and exchanging the culture liquid for fresh one. The peritoneal macrophages were cultured in the presence of both various concentrations (0.1, 1, 10, $10^2$, $10^3$, $10^4$, $10^5$ or $10^6$ μg/ml) of R-MALP-2 or S-MALP-2 obtained by the method described in example 8 and recombined interferon-γ (rIFN-γ) at a concentration of 30 unit/ml, and production amounts of NO$_2^-$, TNF-α and IL-6 in the culture supernatants were measured (FIG. 22). TNF-α was measured by ELISA (Genzyme) at 3 hours after the onset of the culture, IL-6 was measured by ELISA (ENDOGEN) at 21 hours after the onset of the culture, and NO$_2^-$ was measured by Greiss method using NO$_2$/NO$_3$ assay kit (Dojindo Laboratories) at 46 hours after the onset of the culture. These results indicate that R-MALP-2 shows higher specific activity to peritoneal macrophages than S-MALP-2.

EXAMPLE 15

Responsivenss of Human Monocytes to a Lipoprotein/Lipopeptide

Figure 23:
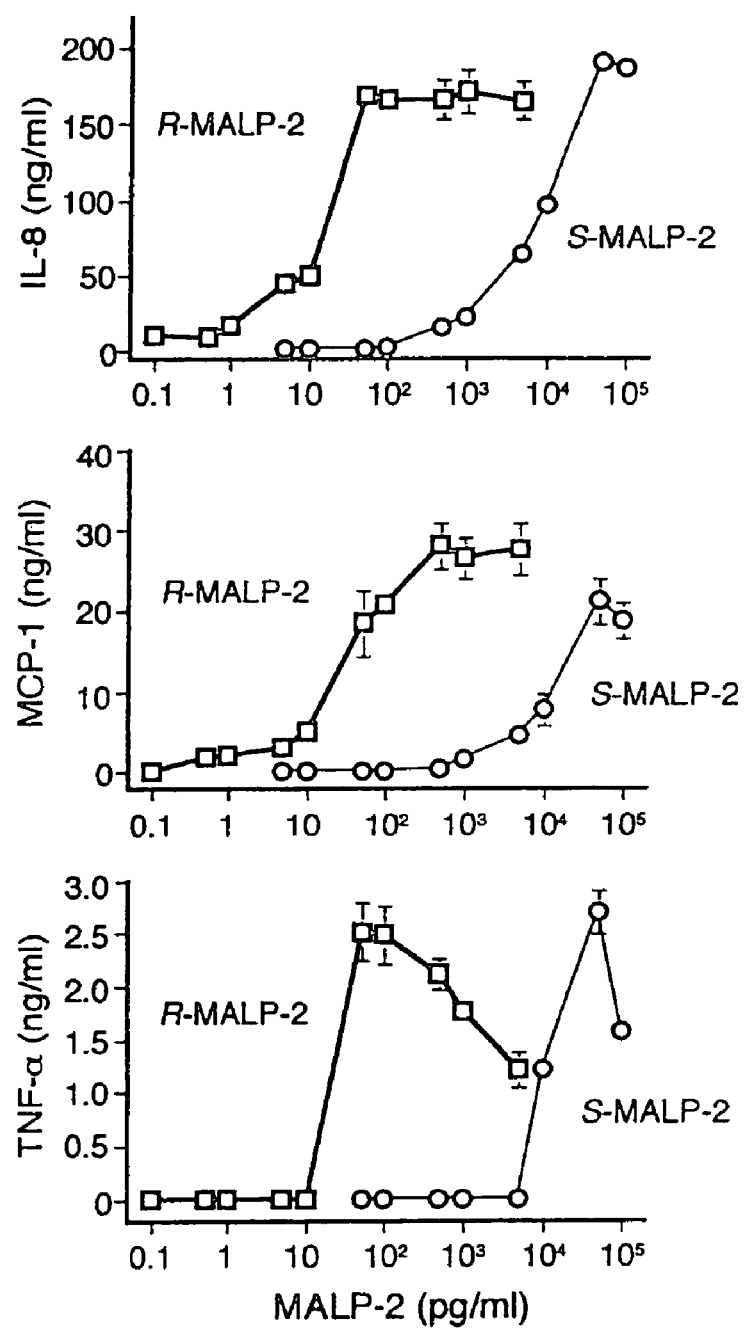
FIG. 23 is a graph showing the results of responsiveness of human monocytes to lipopeptide MALP-2.

Human monocytes from healthy volunteers were washed and used for experiments. With various concentrations (0.1, 1, 10, $10^2$, $10^3$, $10^4$, or $10^5$ μg/ml) of R-MALP-2 or S-MALP-2 obtained by the method in example 13, human monocytes ($7.5\times10^5$) were stimulated for 20 hours. After stimulation, production amounts of IL-8, MCP-1 and TNF-α were measured by ELISA (FIG. 23). The results indicate that R-MALP-2 shows higher specific activity to human monocytes which have not yet differentiated to macrophages or the like than S-MALP-2 as shown in macrophages derived from the mice in example 14.

EXAMPLE 16

Unresponsiveness of TLR2 Knockout Mice to a Lipoprotein/Lipopeptide

Responsiveness of each peritoneal macrophage of wild-type (wild-type), TLR2 knockout (TLR2−/−), TLR4 knockout (TLR4−/−), and MyD88 knockout (MyD88−/−) mice to a lipoprotein/lipopeptide was examined with MALP-2 derived from mycoplasma. Peritoneal macrophages of each mouse were isolated by the method described in example 14, and each of peritoneal macrophages were cultured for 24 hours with various concentrations (0, 0.1, 1, 10, $10^2$, $10^3$, or $10^4$ pg/ml) of R-MALP-2 or S-MALP-2 obtained in example 13, in the presence (FIGS. 24B and D) or absence (FIG. 24 A and C) of rINFγ (30 unit/ml). After the culture, production amounts of TNF-α and NO$_2^-$ in the culture supernatants were measured (FIG. 24).

Figure 24:
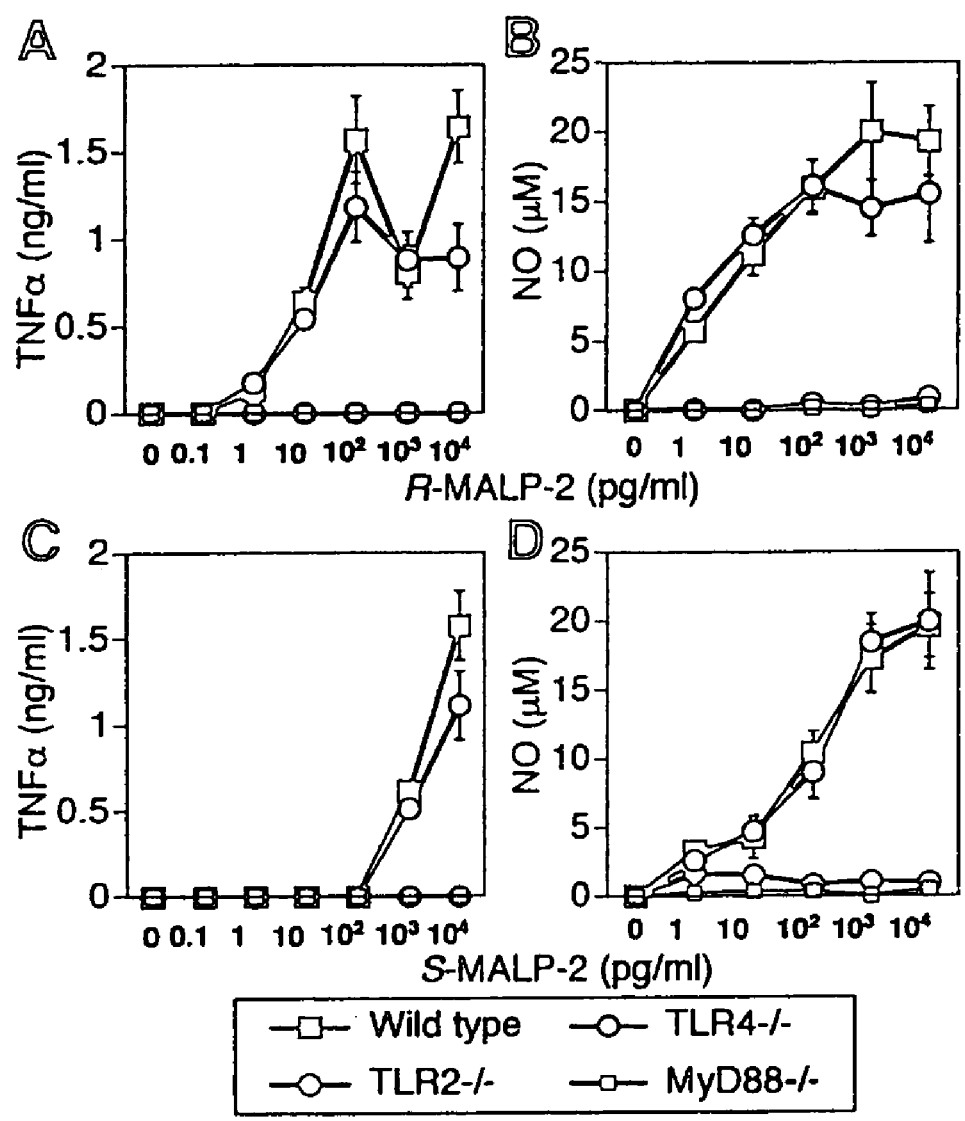
FIG. 24(A–D) is a graph showing the results of responsiveness of peritoneal macrophages of the TLR2 knockout mice, the wild-type mice, the TLR4 knockout mice and the MyD88 knockout mice of the present invention to lipopeptide MALP-2.

The results indicate that production of TNF-α and NO$_2^-$ increased in response to R-MALP-2 in a dose-dependent manner in peritoneal macrophages of wild-type and TLR4-deficient mice, whereas neithor TNF-α nor NO$_2^-$ was produced in those of TLR2- and MyD88-deficient mice (FIG. 24 A and B). Similar results were obtained with S-MALP-2 as well (FIG. 24 C and D). Further, it has been confirmed that peritoneal macrophages of TLR2- and MyD88-deficient mice were unresponsive to R-MALP-2- or S-MALP-2-stimulated IL-6 production (data not shown). Thus indicates that a lipoprotein/lipopeptide derived from mycoplasma, such as R-MALP-2 or the like, activates macrophages via TLR2 and MyD88.

EXAMPLE 17

Figure 25:
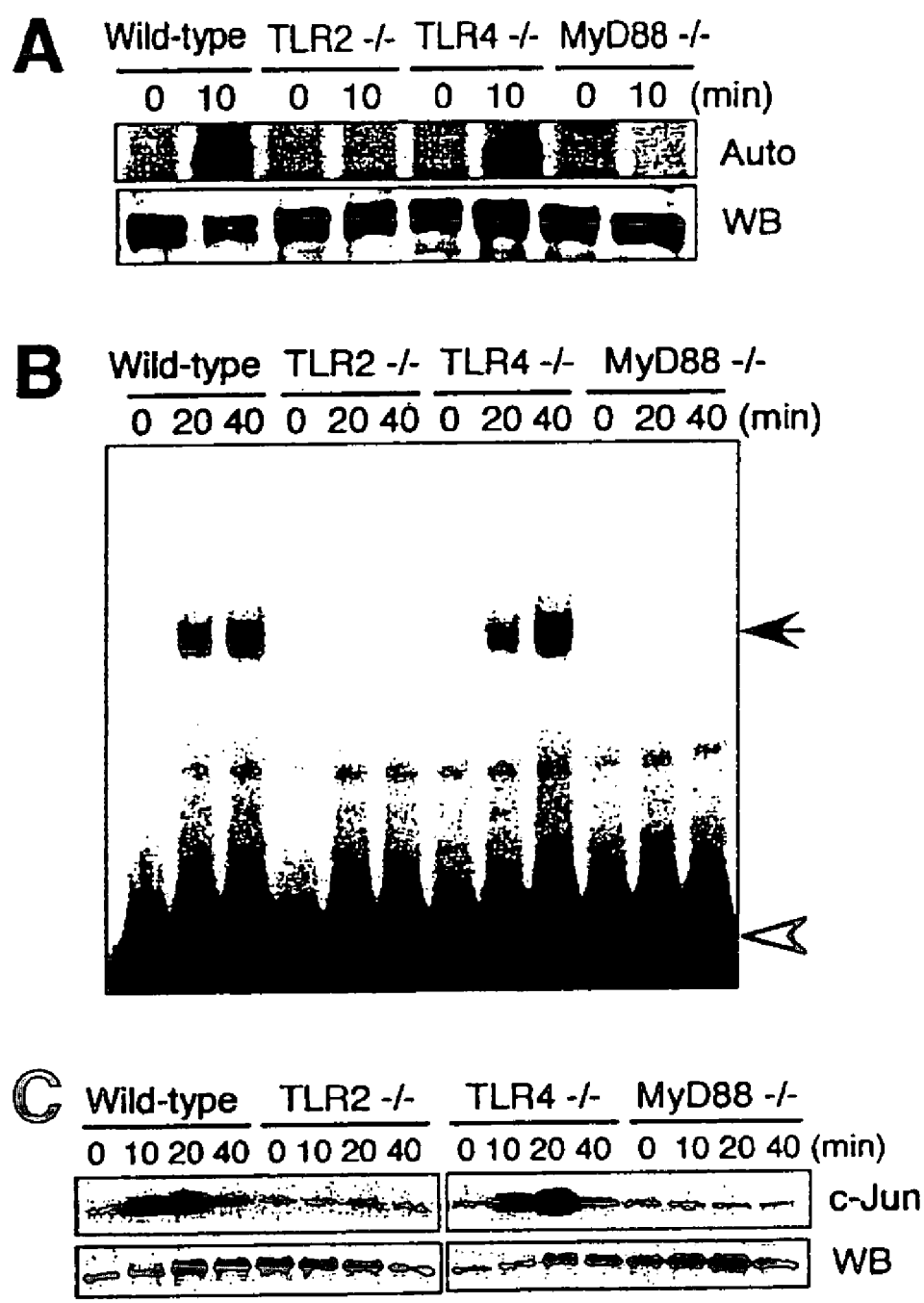
FIG. 25(A–C) is a graph showing the results of lipopeptide MALP-2-stimulated in vitro kinase assay, Western blot analysis and electrophoretic mobility shift assay in the TLR2 knockout mice, the wild-type mice, the TLR4 knockout mice and the MyD88 knockout mice of the present invention.

Lipoprotein/Lipopeptide-Stimulated In Vitro Kinase Assay and Western Blot Analysis In order to examine whether a lipoprotein/lipopeptide activates intracellular signaling molecules with the results of example 16, peritoneal macrophages of the 4 kinds of mouse ($1\times10^6$) were stimulated with 0.3 ng/ml of R-MALP-2 for 10 minutes, and in vitro kinase assay (Auto in FIG. 25A), Western blot analysis (WB in FIG. 25A), electrophoretic mobility shift assay (FIG. 25B) were conducted with anti- IRAK antibody as in example 12. In addition, in vitro kinase assay (Auto in FIG. 25C) and Western blot analysis (WB in FIG. 25C) with anti-JNK1 antibody were also conducted. As a result, activation of IRAK, NF-$_\kappa$B and JNK in response to MALP could not confirmed in macrophages of TLR2 and MyD88 knockout mice. These results indicate that the lipoprotein/lipopeptide derived from mycoplasma causes vital reaction via TLR2 and MyD88 signaling pathway.

INDUSTRIAL APPLICABILITY

The MyD88 knockout mouse, which is the bacterial cell component-unresponsive model animal of the present invention, is unresponsive to endotoxin derived from Gram-negative bacteria, peptidoglycan derived from Gram-positive bacteria, lipoteichoic acid, *mycobacterium tuberculosis* lysate and other such cell wall components of Gram-positive bacteria, a lipoprotein/lipopeptide and the like, and the TLR2 knockout mouse is unresponsive to peptidoglycan which is a cell wall component of Gram-positive bacteria and the like, a lipoprotein/lipopeptide and the like, and hyporesponsive to cell wall fractions of Gram-positive bacteria. Therefore, by using these knockout mice, it becomes possible to obtain useful information of signaling receptors of selective components such as peptidoglycan which is a cell wall component of Gram-positive bacteria, a lipoprotein/lipopeptide and the like, to conduct screenings of a promoter or a suppressor of bacterial infection, a promoter or a suppressor of responsiveness to bacterial cell components such as an agonist, an antagonist to TLR2 or the like, to evaluate endotoxin activity, IL-1 activity and IL-18 activity in subject materials, and to detect bacterial cell components in subject materials, and consequently, it becomes possible to obtain useful information for development of medicines for diseases caused by excessive production of bacterial cell wall components such as endotoxin and the like, IL-1, IL-18 or receptors of these materials and the like, and for elucidating molecular mechanism in a process of infection by bacteria such as *Mycoplasma, Spirochaeta* and the like, and for development of new remedies for infections.

What is claimed is:

1. A mouse comprising homozygous disruption of TLR2 gene in its genome, wherein such disruption results in no production of endogenous TLR2 protein, and wherein said mouse exhibits the phenotype of being unresponsive to bacterial cell component(s) that is a lipoprotein/lipopeptide.

2. The mouse according to claim 1, wherein a lipoprotein/lipopeptide is a macrophage-activating lipopeptide obtained from bacteria which belong to *Mycoplasma*.

3. The mouse according to claim 1 that is further unresponsive to peptidoglycan as a bacterial cell component.

4. The mouse according to claim 1 that is further hyporesponsive to a cell wall fraction of Gram-positive bacteria.

5. A mouse comprising homozygous disruption of MyD88 gene in its genome, wherein such disruption results in no production of endogenous MyD88 protein, and wherein said mouse exhibits the phenotype of being unresponsive to bacterial cell component(s) that is a lipoprotein/lipopeptide.

6. The mouse according to claim 5, wherein a lipoprotein/lipopeptide is a macrophage-activating lipopeptide obtained from bacteria which belong to *Mycoplasma*.

7. The mouse according to claim 5 that is further unresponsive to peptidoglycan as a bacterial cell component.

8. The mouse according to claim 5 that is further unresponsive to a cell wall fraction of Gram-positive bacteria.

9. The mouse according to claim 5 that is further unresponsive to endotoxin as a bacterial cell component.

10. The mouse according to claim 5 that is further unresponsive to lipoteichoic acid as a bacterial cell component.

11. The mouse according to claim 5 that is further unresponsive to *Mycobacterium tuberculosis* lysate as a bacterial cell component.

* * * * *